United States Patent
Suzuki et al.

(10) Patent No.: US 6,307,210 B1
(45) Date of Patent: Oct. 23, 2001

(54) DEVICE FOR IMAGING OBJECT TO BE INSPECTED AND DEVICE FOR INSPECTING SEMICONDUCTOR PACKAGE

(75) Inventors: Yasuyoshi Suzuki, Fujisawa; Yoshihiko Nakakoji, Hiratsuka; Toru Inomoto, Chigasaki; Kazuyuki Kimura, Yokohama; Masashi Higashi, Fujisawa, all of (JP)

(73) Assignee: Cognex Technology and Investment Corporation, Mountain View, CA (US)

( * ) Notice: Subject to any disclaimer, the term of this patent is extended or adjusted under 35 U.S.C. 154(b) by 0 days.

(21) Appl. No.: 09/254,684

(22) PCT Filed: Sep. 17, 1997

(86) PCT No.: PCT/JP97/03284

§ 371 Date: Mar. 16, 1999

§ 102(e) Date: Mar. 16, 1999

(87) PCT Pub. No.: WO98/12502

PCT Pub. Date: Mar. 26, 1998

(30) Foreign Application Priority Data

Sep. 17, 1996 (JP) .................................................. 8-245173
Jun. 13, 1997 (JP) .................................................. 9-157049

(51) Int. Cl.⁷ .................................................. H01L 23/48
(52) U.S. Cl. .............................. 250/559.08; 250/559.34; 257/697
(58) Field of Search ................... 250/559.08, 559.07, 250/559.09, 559.34, 559.44; 257/678, 690, 692, 693, 697; 438/123; 324/765, 755

(56) References Cited

U.S. PATENT DOCUMENTS

| | | | |
|---|---|---|---|
| 5,212,390 | * | 5/1993 | LeBeau et al. .................. 250/559.08 |
| 5,866,941 | * | 2/1999 | Lacap .................................... 257/697 |

FOREIGN PATENT DOCUMENTS

| | | |
|---|---|---|
| 52-26844 | 2/1977 | (JP) . |
| 63-113518 | 5/1988 | (JP) . |
| 6-160057 | 6/1994 | (JP) . |
| 7-98216 | 4/1995 | (JP) . |
| 8-29146 | 2/1996 | (JP) . |

OTHER PUBLICATIONS

International Search Report in PCT/JP97/03284 mailed Dec. 24, 1997.

* cited by examiner

Primary Examiner—John R. Lee
Assistant Examiner—Kevin Pyo
(74) Attorney, Agent, or Firm—Varndell & Varndell, PLLC

(57) ABSTRACT

An inspection object imaging device, which images a plurality of objects to be inspected that are located at different imaging distances from imaging means, in which a light transmitting optical member which has a predetermined refractive index and a thickness and which absorbs the differences of the imaging distances is provided in an optical path between the objects to be inspected and the imaging means. When the objects whose optical path lengths from the imaging means are different are imaged by one imaging means, all the objects can be focused simultaneously, so that the time required for the imaging can be reduced and, further, a high quality image can be obtained over the whole imaged region.

13 Claims, 28 Drawing Sheets

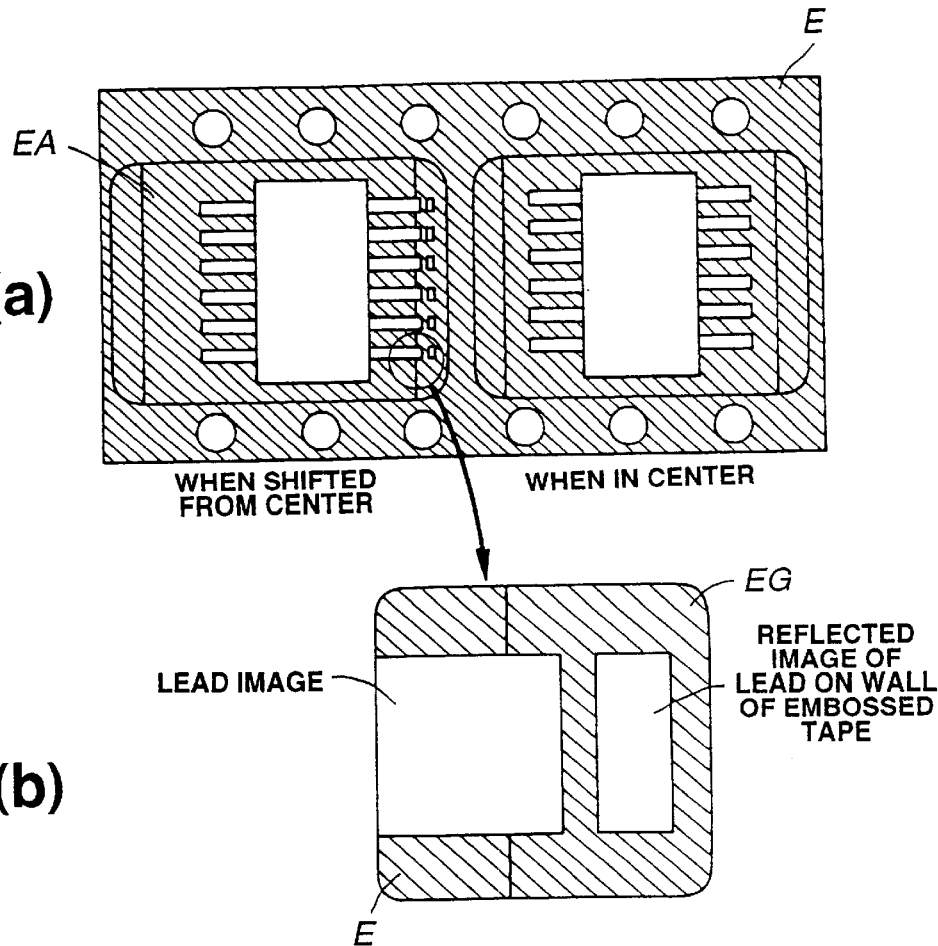
FIG.11(a)
FIG.11(b)
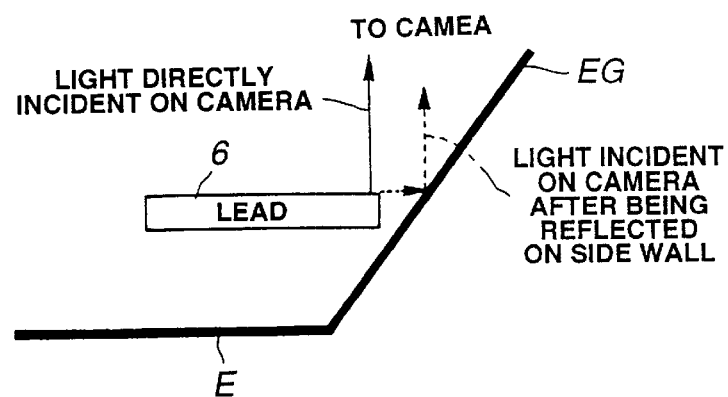
FIG.11(c)

CAMERA IMAGE

DEVICE FOR IMAGING OBJECT TO BE INSPECTED AND DEVICE FOR INSPECTING SEMICONDUCTOR PACKAGE

TECHNICAL FIELD

The present invention relates to a device for imaging an object to be inspected, and a device for inspecting a semiconductor package, which inspects an object to be inspected, such as a semiconductor package, using visual camera means.

BACKGROUND ART

When performing inspection, shape recognition, and other such processing by image processing a picture of an object to be inspected taken with a CCD camera, focusing the CCD camera on the object to be inspected is essential for performing imaging with good accuracy.

However, when imaging different surfaces of an object to be inspected, and when the optical path lengths from a plurality of objects to be inspected to a CCD camera differ, if the camera is focused on a portion of the objects to be inspected, other portions thereof are out of focus.

In other words, the problem, as shown in FIG. 33, is that when attempting to image with 1 CCD camera 2 planes A, B that are different distances from the CCD camera, if the camera is focused on plane A, then the pattern of plane B is out of focus.

Further, the inspection of a semiconductor package is an inspection that uses an imaging device such as the above-mentioned CCD camera. As inspection items of this semiconductor package, there are:

(1) Inspecting the coplanarity of leads;

(2) Inspecting for lead pitch variations, displacement; and (3) Inspecting for missing characters, blurring, and displacement of marks stamped on the upper surface of a package.

Here, when inspecting the coplanarity of the leads of an IC package, such as a surface mount-type SOP (small outline package), an IC side image, which images an IC from the side as shown in FIG. 35(b), is required (to find IC that have lifted leads as shown in FIG. 34).

Accordingly, when performing a lead coplanarity inspection such as this, in the past, a camera was provided to the side of an IC as shown in FIG. 35(a). The technique, whereby a camera is provided to the side of an IC like this, enables an IC image to be suitably captured when the IC is placed on top of a flat tray.

However, when an IC is contained in embossed tape E as shown in FIG. 36, it is impossible to obtain an IC side image by providing a camera to the side of the IC. Embossed tape E is used here to stock a plurality of ICs following production thereof, and is made from a black plastic material. Further, a square-shaped step is formed so as to enable each IC to be housed separately in a plurality of juxtaposed IC containers EA. Furthermore, when stocking ICs, embossed tape E is wound on a reel.

That is, when embossed tape is utilizes as an IC stocker, a process is established so that an IC can be housed in embossed tape following production, but when performing a lead coplanarity inspection in accordance with conventional technology, the need to add a process in which an IC is placed on top of a flat tray so that a camera can be provided to the side of the IC is disadvantageous from the standpoint of production efficiency. Accordingly, an inspection technique for enabling a lead coplanarity inspection to be performed in a state in which an IC is housed as-is in the embossed tape is desirable.

However, as described above, there are other inspections involved in a semiconductor package inspection beside the lead coplanarity inspection, such as inspecting for missing characters, blurring and displacement of the markings stamped on the upper surface of a package. To carry out these inspections, a plan view of the upper surface of a semiconductor package is required. Accordingly, in the past, the trouble was that since cameras were provided both to the side and above a semiconductor, and each of the above-mentioned inspections was performed on the basis of image data of these cameras, numerous cameras were required, costs were high, a lot of space was required for the cameras, and it was difficult to adjust numerous cameras properly.

With the foregoing in view, it is an object of the present invention to provide an inspection object imaging device, which makes it possible to reduce the time required for imaging, and to obtain a high quality image of an entire imaging area, by enabling all objects to be inspected to be brought into focus simultaneously when imaging with 1 imaging means a plurality of objects to be inspected that have different optical path lengths to the imaging means.

A further object of the present invention is to provide a semiconductor package inspection device, which is capable of performing a coplanarity inspection of lead portions even when a semiconductor package is housed in a storage container.

A further object of the present invention is to provide a semiconductor package inspection device, which is capable of performing a lead coplanarity inspection of a semiconductor package based solely on an image by 1 camera provided either almost directly above or directly below the package surface of a semiconductor package.

A further object of the present invention is to provide a semiconductor package inspection device, which is capable of performing an upper surface inspection and a side lead portion inspection of a semiconductor package using 1 imaging means.

DISCLOSURE OF THE INVENTION

The present invention is an inspection object imaging device, which images a plurality of objects to be inspected that are located at different imaging distances from imaging means, characterized in that a light transmitting optical member having a predetermined refractive index and a thickness, which absorbs a difference of the various imaging distances, is disposed in an optical path between the objects to be inspected and the imaging means.

In accordance with this present invention, since a light transmitting optical member is disposed between a plurality of objects to be inspected and an imaging means, and absorbs the imaging distance difference between each object to be inspected and the imaging means, the optical path length to each object to be inspected becomes substantially the same, enabling all objects to be inspected to be brought into focus at the same time. Consequently, in accordance with the present invention, the imaging time for a plurality of objects to be inspected can be shortened, and efficient imaging can be performed.

Further, the present invention is an inspection object imaging device, which images an upper surface and a side surface of an object to be inspected with one imaging means provided above the object to be inspected, characterized in that a light transmitting optical member having a predetermined refractive index is provided to the side of the object to be inspected, and a thickness of the optical member is set to a value, which absorbs an optical path length difference between an optical path from the upper surface of the object to be inspected to the imaging means and an optical path from the side of the object to be inspected via the optical member to the imaging means.

In accordance with this present invention, since a light transmitting optical member, having a predetermined refractive index, is provided to the side of an object to be inspected, and, in accordance with the optical member, the optical path length difference between the optical path from the upper surface of the object to be inspected to the imaging means, and the optical path from the side of the object to be inspected via the above-mentioned optical member to the imaging means is absorbed, a side and upper surface of the object to be inspected can be brought into focus simultaneously, the imaging time for an object to be inspected can be shortened, and efficient imaging can be performed.

Further, the present invention is a semiconductor package inspection device, which inspects a coplanarity of leads of a semiconductor package, characterized in that the semiconductor package inspection device comprises: imaging means for imaging a lead portion of the semiconductor package from diagonally above at a predetermined angle; and inspecting means for inspecting the coplanarity of leads of the semiconductor package on the basis of image data of the imaging means.

In accordance with this present invention, since imaging of a lead portion of a semiconductor package is performed from diagonally above at a predetermined angle, and inspection of the coplanarity of leads of the semiconductor package is performed on the basis of the image data thereof, lead coplanarity inspection can be carried out in a state in which a semiconductor package is housed in a storage container, such as embossed tape, and in accordance therewith, it is not necessary to place a semiconductor package on top of a flat tray each time for inspection, enabling inspection work to be shortened.

Further, the present invention is a semiconductor package inspection device, which images an upper surface and a side lead portion of a semiconductor package, and inspects the semiconductor package on the basis of image data thereof, characterized in that the semiconductor package inspection device comprises: one visual camera means, which is provided above the semiconductor package, an imaging axis thereof being set at a proximate right angle relative to the upper surface of the semiconductor package, and the upper surface of the semiconductor package being set so that it is located in a center region of a field of view area thereof; and a light transmitting optical member, which has a predetermined refractive index, and which is provided between the semiconductor package and the visual camera means, a lead portion of the semiconductor package being imaged from diagonally above at a predetermined angle by the visual camera means, and an image thereof being guided to an edge portion region of the field of view area of the visual camera means, and in that a thickness of the light transmitting optical member is set at a value, which absorbs an optical path length difference between an optical path from the upper surface of the semiconductor package to the visual camera means, and an optical path from the side lead portion via the light transmitting optical member to the visual camera means.

In accordance with the present invention, since one visual camera means is provided above a semiconductor package, and an upper surface image and a lead portion image are imaged simultaneously by this one camera, and a light transmitting optical member is disposed between the above-mentioned semiconductor package and the above-mentioned visual camera means, and absorbs the optical path length difference between the optical path from the upper surface of the semiconductor package to the visual camera means, and the optical path from the above-mentioned side lead portion via this light transmitting optical member to the above-mentioned visual camera means, a side and upper surface of a semiconductor package can be brought into focus simultaneously at imaging, semiconductor package imaging time can be shortened, and efficient imaging can be performed.

Further, the present invention is a semiconductor package inspection device, which inspects a coplanarity of leads of a semiconductor package, characterized in that the semiconductor package inspection device comprises: one visual camera means, which is provided either above or below the semiconductor package, an imaging axis thereof being set at a proximate right angle relative to an upper surface of the semiconductor package; light guiding means, which is provided between the semiconductor package and the visual camera means, for guiding an image of a lead portion of the semiconductor package within a field of view of the visual camera means so that the lead portion of the semiconductor package is imaged from at least two different directions by the visual camera means; and inspection means for inspecting on the basis of image data of the imaging means the coplanarity of the leads of the semiconductor package using a triangulation method.

In accordance with this present invention, since a light guiding means, such as a prism, is disposed between a semiconductor package, and one visual camera means provided either above or below this semiconductor package, and the lead portion of the semiconductor package can be imaged by the 1 visual camera means from at least 2 different directions, it is possible to perform coplanarity inspection of a lead portion in the height direction using a triangulation method based on a image in accordance with only one camera, and in accordance therewith, the system constitution can be made compact and inexpensive, and the computing speed thereof can also be enhanced.

BRIEF DESCRIPTION OF THE DRAWINGS

FIGS. 11(a) to 11(c) are diagrams illustrating the inconveniences of prior art;

BEST MODE FOR CARRYING OUT THE INVENTION

A detailed description of the embodiments is provided hereinbelow in accordance with the accompanying figures.

Figure 1:
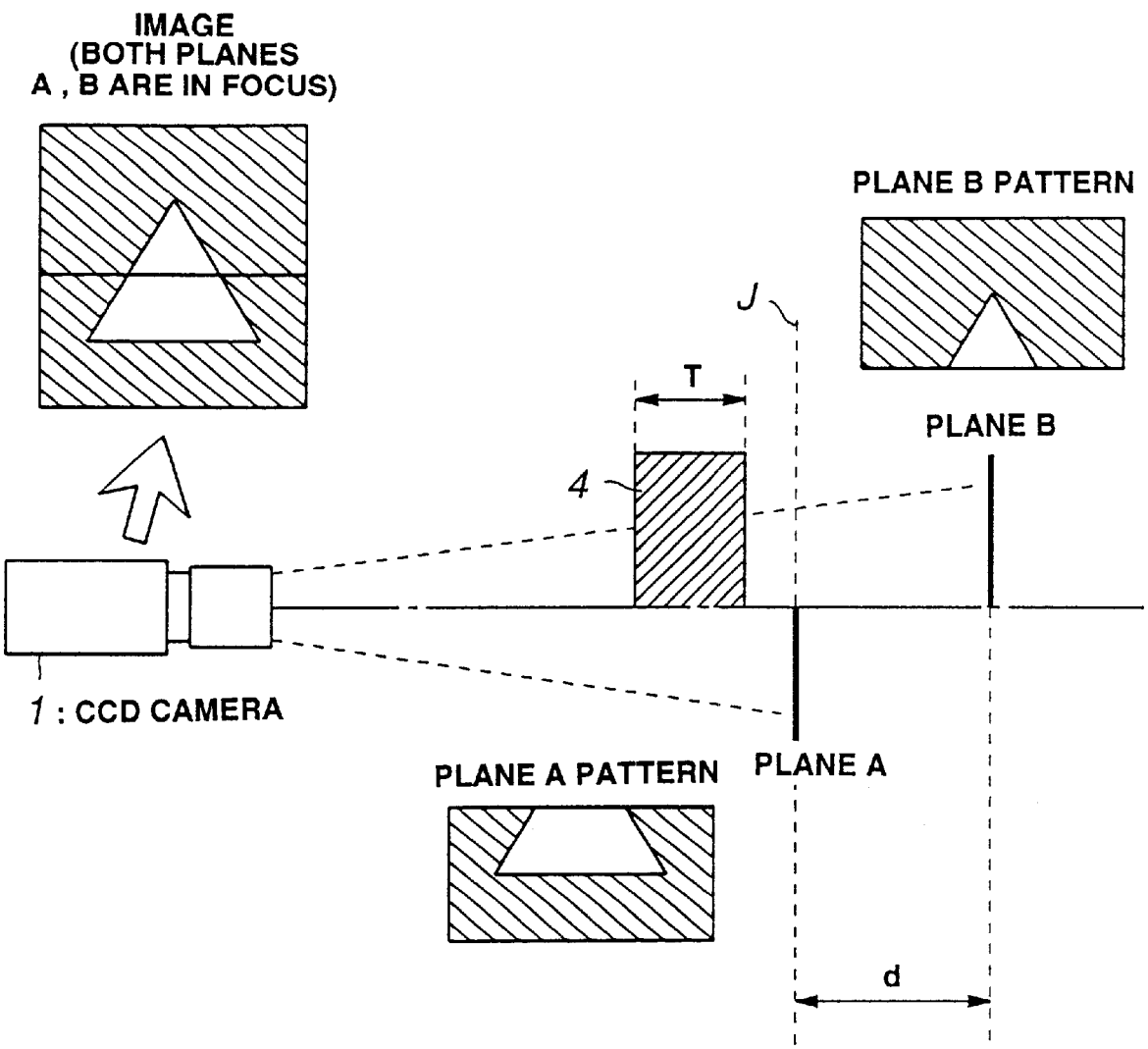
FIG. 1 is a diagram showing a first embodiment of the present invention.

FIG. 1 shows a first embodiment of the present invention. This first embodiment shows, in principle, one concept of the present invention.

In FIG. 1, a CCD camera 1 images 2 planes A, B that are different distances from the camera 1. The distance between these planes A, B is represented by d.

Here, an optical member 4 comprising, for example, quartz glass, which has high light transmissivity, and a refractive index R which differs from that of air (R>1, in this case), is disposed on the optical path between the camera 1 and plane A, which is a long distance from the camera 1, and in accordance with the disposition of this optical member 4, the difference of the imaging distances of planes A, B is absorbed.

If the thickness of the optical member 4 is designated as T, the optical thickness of this member 4 becomes T/R when converted to air (the refractive index of air is set at 1). Therefore, when imaging surface J, which is the focal point of the CCD camera 1 in FIG. 1, is located at plane A, if the optical member 4 is disposed between the CCD camera 1 and plane B, the imaging surface location in this case is only $T(1-(1/R))$ away from plane B.

For this reason, if it is assumed that the imaging surface location with regard to plane B is only the distance d from plane A, it is possible to realize by disposing an optical member 4 between CCD camera 1 and plane B, which can be stipulated as $$d=T(1-(1/R))$$

If we solve for T in the above equation, we arrive at the following equation (1).

$$T=dR/(R-1) \qquad (1)$$

Therefore, in this first embodiment, an optical member of a thickness T, which realizes the above equation (1), is inserted between an object to be inspected and a camera 1, the difference in the length of the optical path to each object to be inspected is absorbed, and all the objects to be inspected can be brought into focus simultaneously.

Here, if we make d=5 mm, and assume that the optical member 2 is quartz glass, since the refractive index thereof is R=1.5168, and since $$T=14.7$$

then a quartz glass of roughly 15 mm can be provided.

FIG. 2 is diagrams of a second embodiment of the present invention.

Figure 2A:
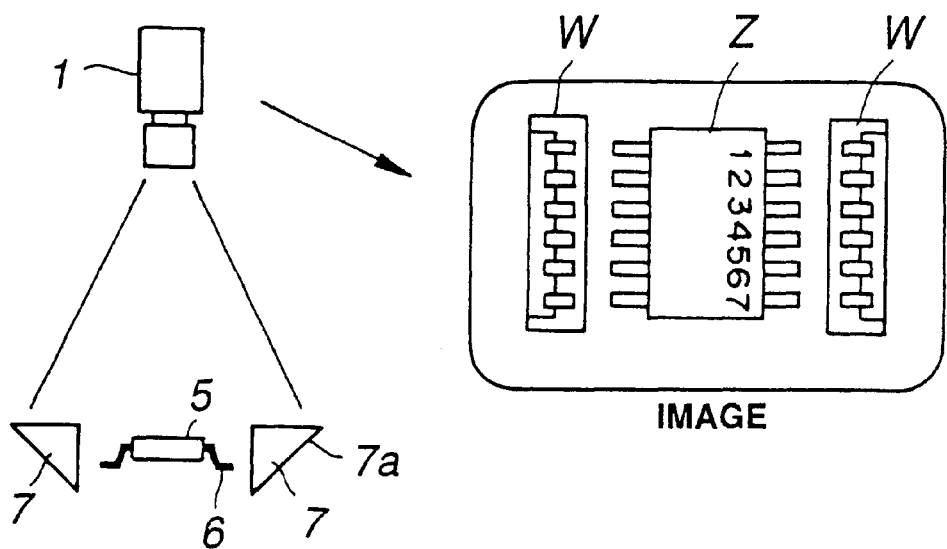
FIGS. 2(a) and 2(b) are diagrams showing a second embodiment of the present invention.
Figure 2B:
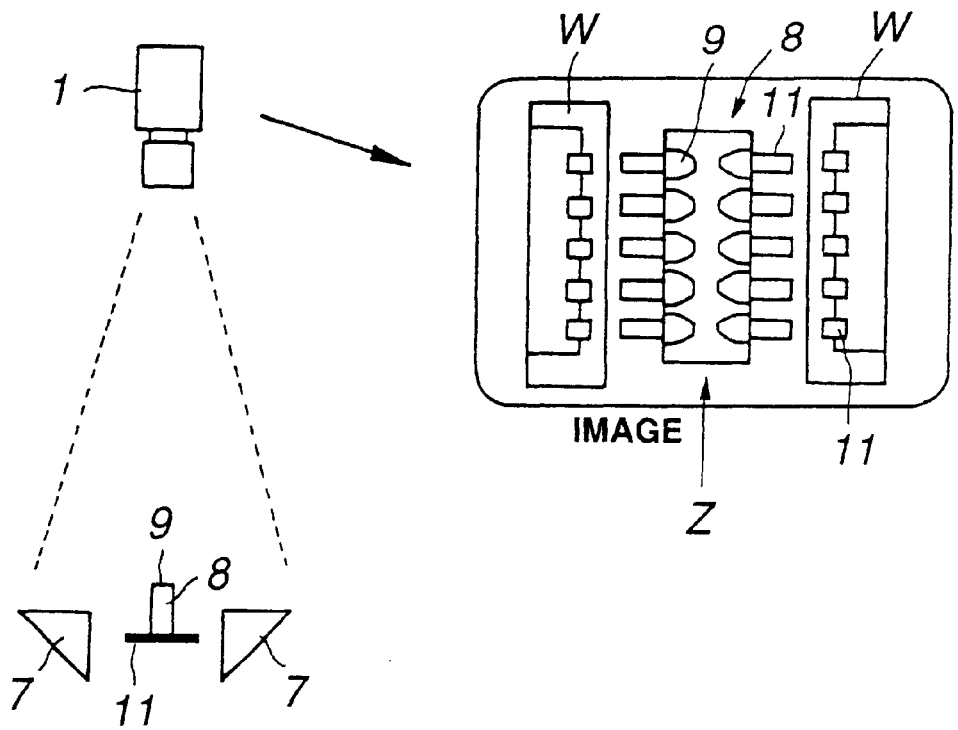

The embodiment of FIG. 2(a) shows the above-mentioned first embodiment applied to the inspection of an IC package (SOP), and the embodiment of FIG. 2(b) shows the first embodiment applied to the inspection of leaded connectors.

That is, in FIG. 2(a), an inspection of missing characters and the like in the markings stamped on the SOP upper surface, and an inspection of the coplanarity of leads 6 are performed based on image data of 1 CCD camera provided above a SOP 5 having gullwing-shaped leads 6, for which an upper surface image Z and a side image W of the SOP 5 are required.

Here, the upper surface image of the SOP 5 can be imaged by a camera 1 as-is, but a side image of the SOP 5 cannot be imaged as-is by the camera 1. Accordingly, in this second embodiment, a prism mirror, comprising quartz glass, and having a reflective surface 7a, is provided on both sides of the SOP 5.

Further, in the case of this constitution, because there is a difference between the optical path length from the upper surface of SOP 5 to camera 1, and the optical path length from the side of SOP 5 via prism mirror 7 to camera 1, the thickness of prism mirror 7 is set to a value calculated based on the above equation (1) of the first embodiment so as to absorb the difference in the above-mentioned optical path lengths.

In this manner, in accordance with this embodiment, since an upper surface image and a side image of an IC package 5 can be imaged on the same screen by 1 camera 1, and focusing can be performed for both of these images at that time, it is possible to enhance both inspection accuracy and inspection speed.

Next, in FIG. 2(b), an inspection of a gap (mating portion) 9 formed in the upper surface of a connector 8, and an inspection of the coplanarity of mounting leads 11 are performed based on image data of 1 CCD camera 1 provided above a leaded connector 8, for which, similar to the embodiment of FIG. 2(a), an upper surface image Z and a side image W of a connector 7 are required.

Therefore, in this FIG. 2(b) embodiment as well, a prism mirror 7 is provided to the side of a connector 8, and the thickness of this prism mirror 7 is set to a value calculated based on the above equation (1) of the first embodiment so as to absorb the difference in the optical path lengths.

Figure 3:
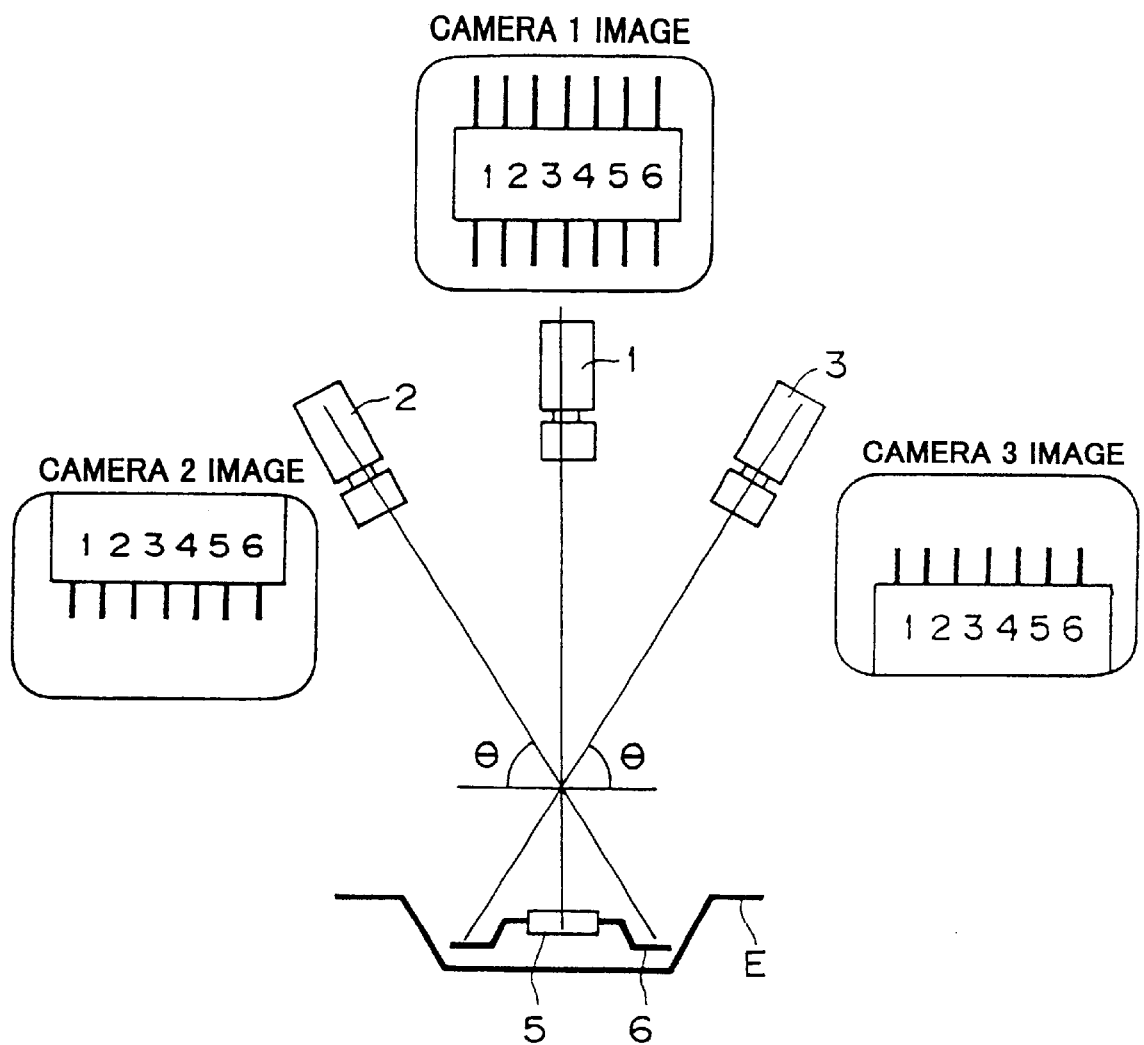
FIG. 3 is a diagram showing a third embodiment of the present invention.

FIG. 3 shows a third embodiment of the present invention. From the third embodiment shown in FIG. 3 to the fifteenth embodiment shown in FIG. 18, it is assumed that an IC package (a SOP in this case) 5 is housed in the above-described embossed tape E, and in this state, a side image of SOP 5 required for inspecting the lead coplanarity of SOP 5 cannot be imaged by providing a camera directly opposite the side of SOP 5. Further, under circumstances like this, a prism mirror 6 cannot be provided to the side of SOP 5 as in the above second embodiment.

Accordingly, in this third embodiment, the leads 6 of SOP 5 are imaged by CCD cameras 2, 3, which image from diagonally above at predetermined angles θ, and the inspection of lead 6 coplanarity is performed based on the image data thereof.

Furthermore, the upper surface image of SOP 5 is imaged by a camera 1 provided directly above SOP 5 as usual, and inspection of the markings stamped on the upper surface of SOP 5 is performed based on the image data thereof.

Figure 4:
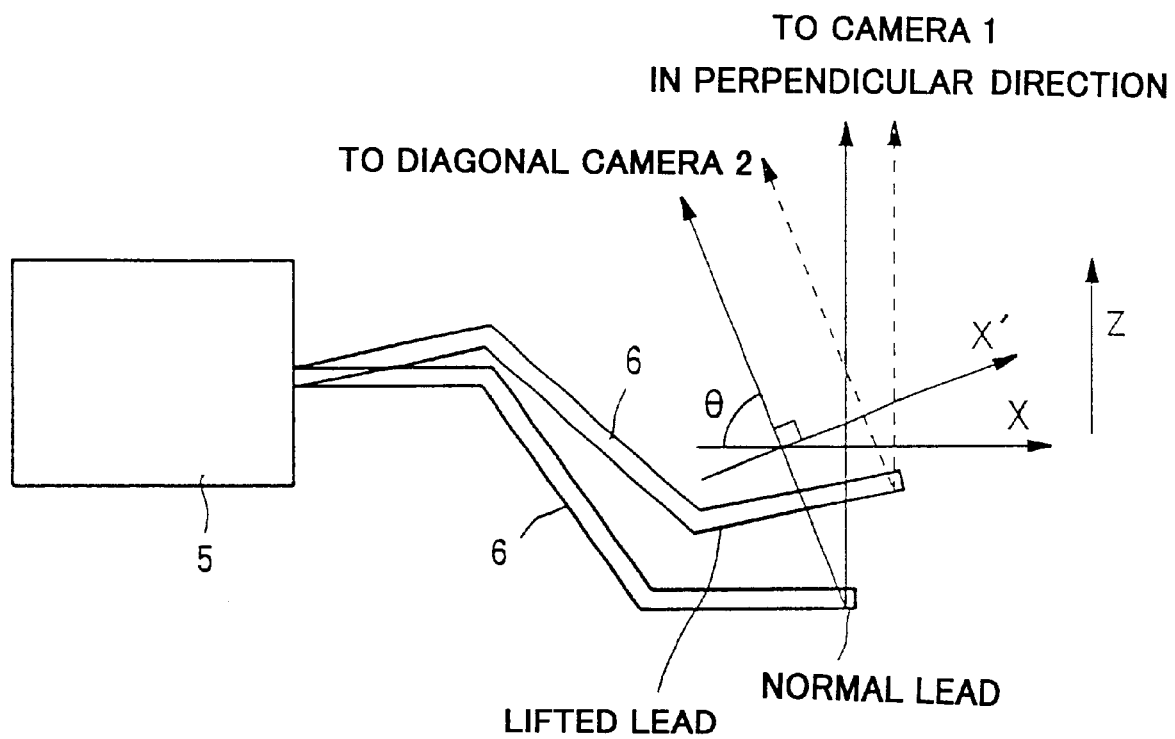
FIG. 4 is a diagram illustrating operation in accordance with the third embodiment.

That is, in this third embodiment, because the location of the tip of a lead in the x' direction differs between a lifted lead and a normal lead as shown in FIG. 4, a coplanarity inspection of the leads 6 can be performed by imaging and detecting this by camera 2 from a diagonal direction.

Furthermore, in this case, since the displacement of a lifted lead from a normal lead in the x direction can be detected even if a camera 1 provided above SOP 5 images the leads 6, if a coordinate location of a lead 6 in the z direction is calculated based on the image data of these cameras 1 and 2, a more accurate inspection can be achieved than with camera 2 alone.

Figure 5:
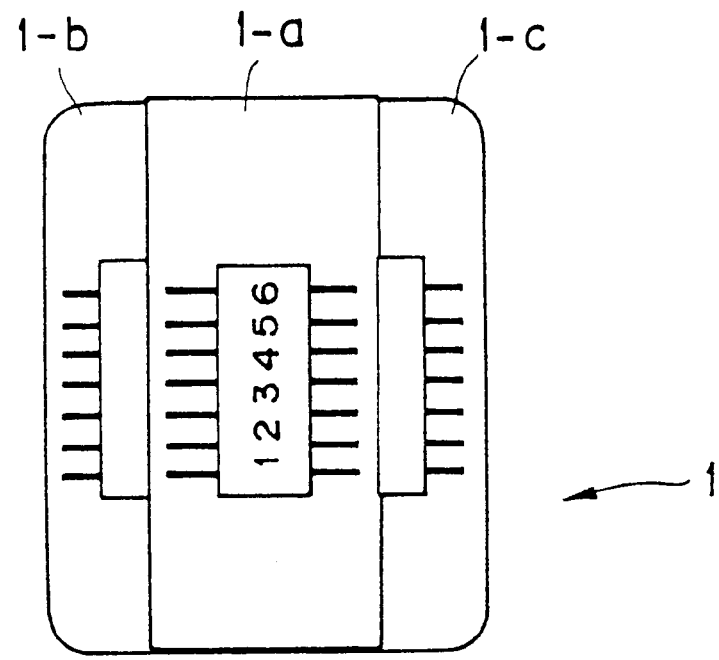
FIG. 5 is a diagram showing a fourth embodiment of the present invention.
Figure 5:
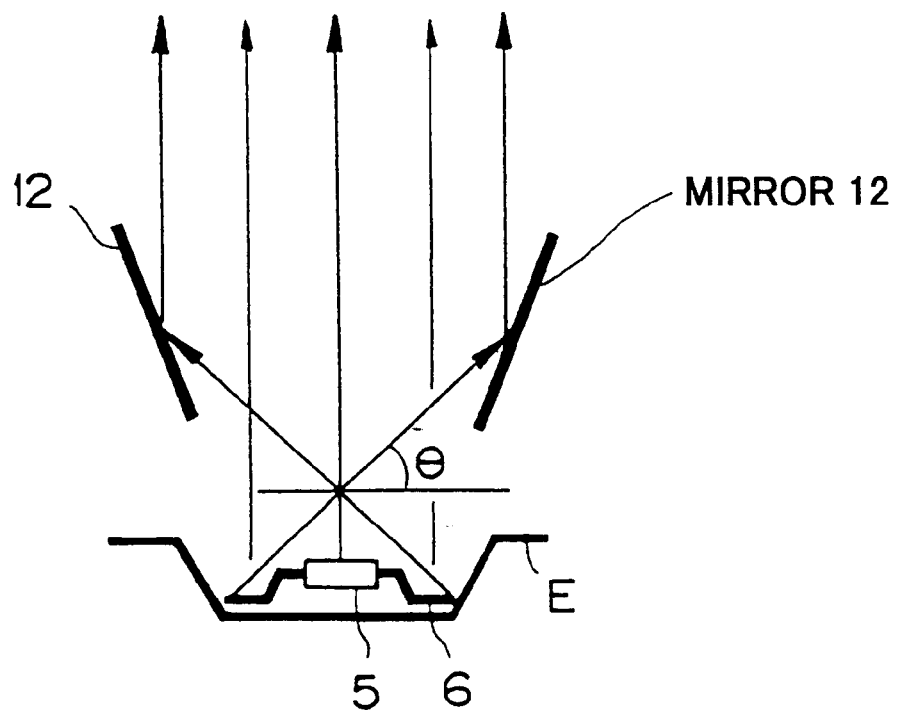

FIG. 5 shows a fourth embodiment of the present invention.

In this fourth embodiment, the inspection of the stamped markings on the upper surface of a SOP 5 and the inspection of lead coplanarity carried out in the above third embodiment are performed using 1 CCD camera 1.

That is, in this case, the upper surface image of SOP 5 is imaged from directly above in the center region 1-$a$ of the field of view area of the camera 1, and the configuration location and configuration angle of a mirror 12 are adjusted so that the lead portion 6 of SOP 5 can be imaged at a predetermined angle θ in the edge regions 1-$b$, 1-$c$ of the field of view area of the camera 1. Therefore, a lead portion image of SOP 5 that is substantially the same as that of the above third embodiment can be obtained with this fourth embodiment as well.

In this manner, in this embodiment, the center portion 1-$a$ of the field of view area of CCD camera 1 is used as the surface image for inspecting the marking of SOP 5, and the side edge portions 1-$b$, 1-$c$ of the field of view area of the same CCD camera 1 are used as the images for measuring the coplanarity of the leads 6 of SOP 5. Consequently, this embodiment is more advantageous than the above third embodiment from the standpoints of costs, space, and ease of adjusting the camera location.

Further, in this embodiment, which images SOP 5 leads 6 from 2 different directions, since data is obtained in the CCD camera 1 image, it becomes possible to measure using triangulation a coordinate location in the direction of height of the tip of each lead by using the image data thereof. That is, in this embodiment, it is possible to carry out with a high degree of accuracy using the triangulation method a coplanarity inspection of lead tips using only image data in accordance with 1 camera.

Figure 6:
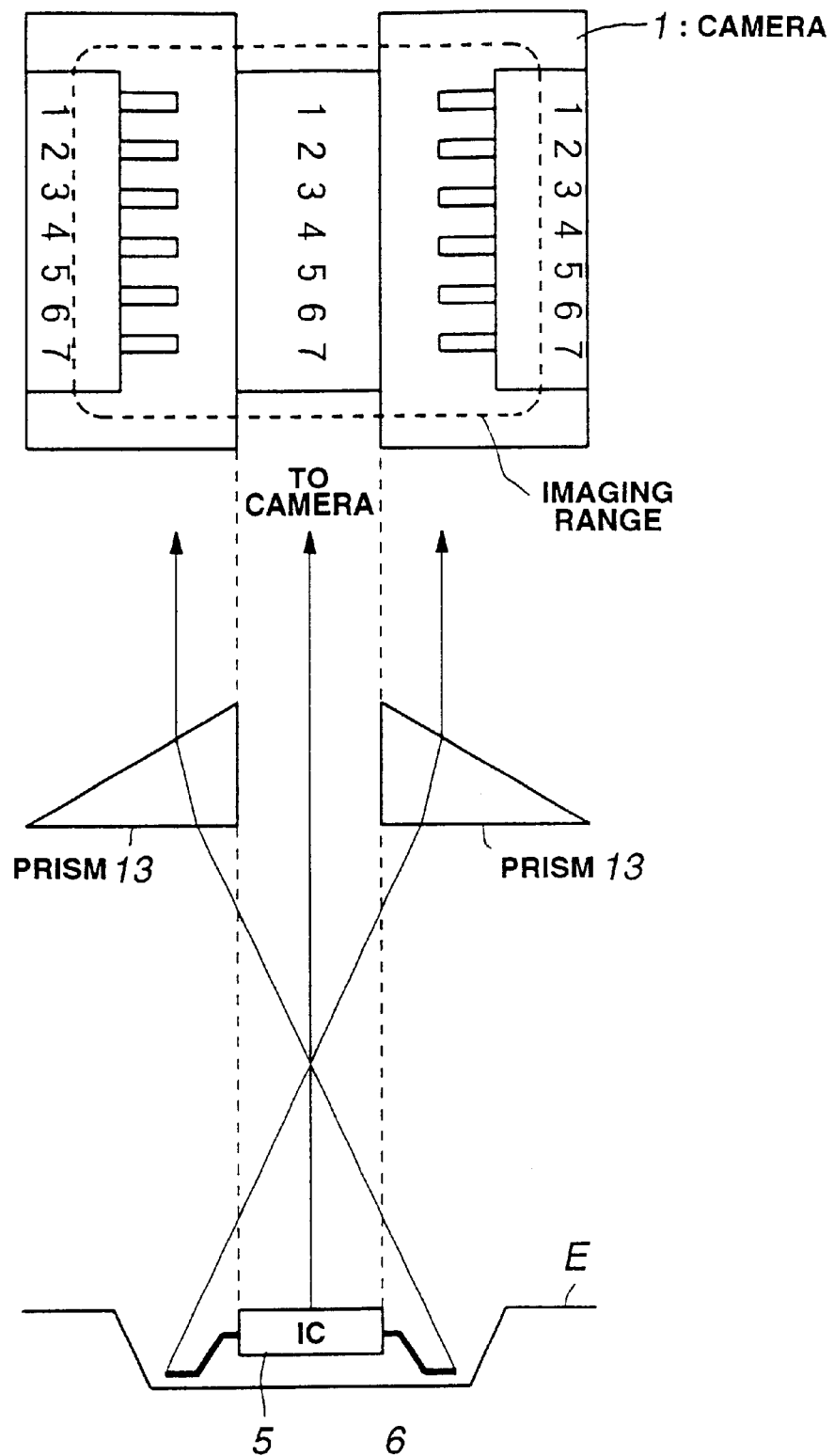
FIG. 6 is a diagram showing a fifth embodiment of the present invention.

FIG. 6 shows a fifth embodiment of the present invention.

In this fifth embodiment, a prism 13 is provided in place of the mirror 12 of the above fourth embodiment, and an image of the lead portion 6 of SOP 5 imaged from diagonally above is guided to a camera 1 by this prism 13. Further, in this embodiment, a space is provided between 2 prisms 13, and the upper surface image of SOP 5 is incident on the camera 1 via the gap thereof.

Therefore, in this embodiment, it is possible to bring both of these imaging objects (SOP upper surface and lead portion) into focus simultaneously by absorbing in accordance with this prism 13 the difference between the optical path length from the SOP 5 upper surface to the camera 1, and the optical path length from the SOP 5 lead portion via the prism 13 to the camera 1. That is, in this case, the thickness and refractive index of the prism 13 is set on the basis of the above equation (1).

Figure 7:
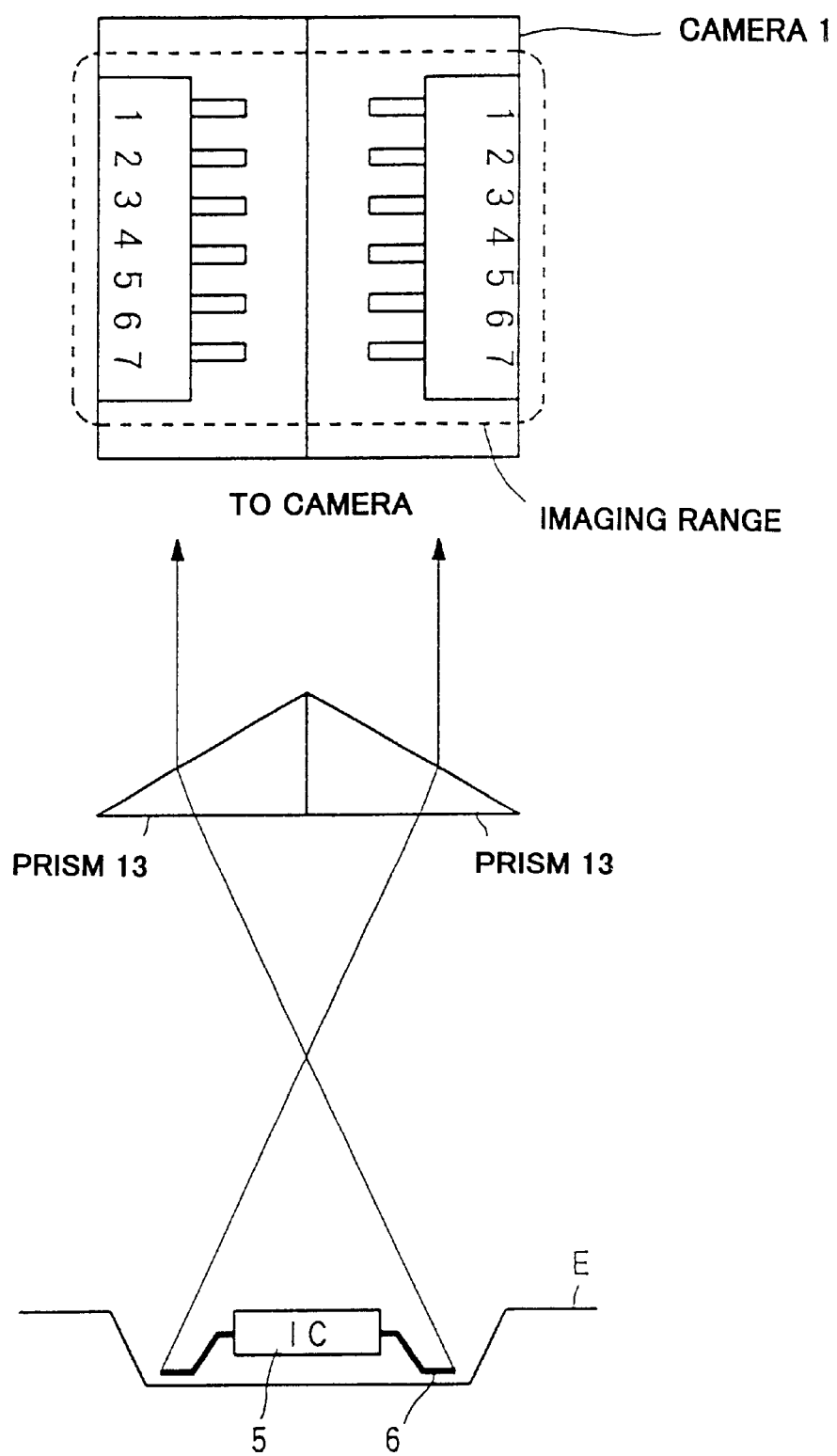
FIG. 7 is a diagram showing a sixth embodiment of the present invention.

FIG. 7 shows a sixth embodiment of the present invention.

In this sixth embodiment, 2 prisms 13 are provided side by side with no space between them, and only the image of the SOP 5 lead portion is incident on a camera 1. That is, in this case, the plan view image of the upper surface of SOP 5 is not incident on the camera 1.

Figure 8:
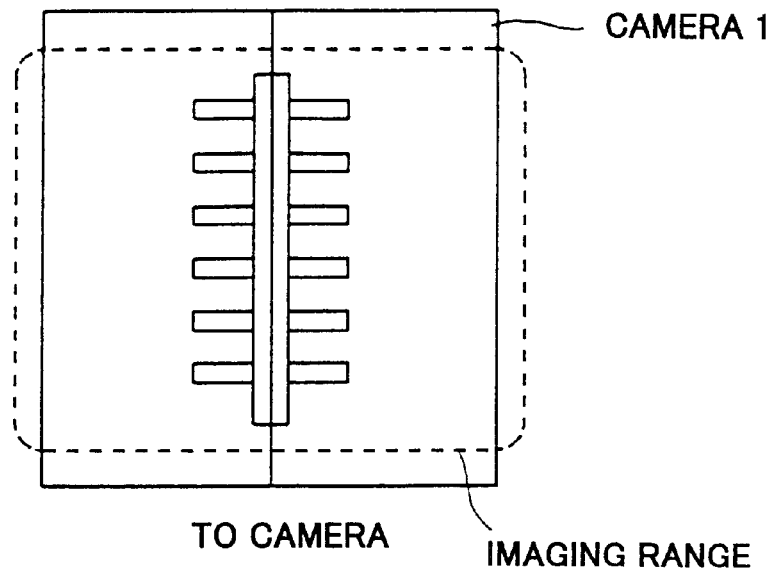
FIG. 8 is a diagram showing a seventh embodiment of the present invention.
Figure 8:
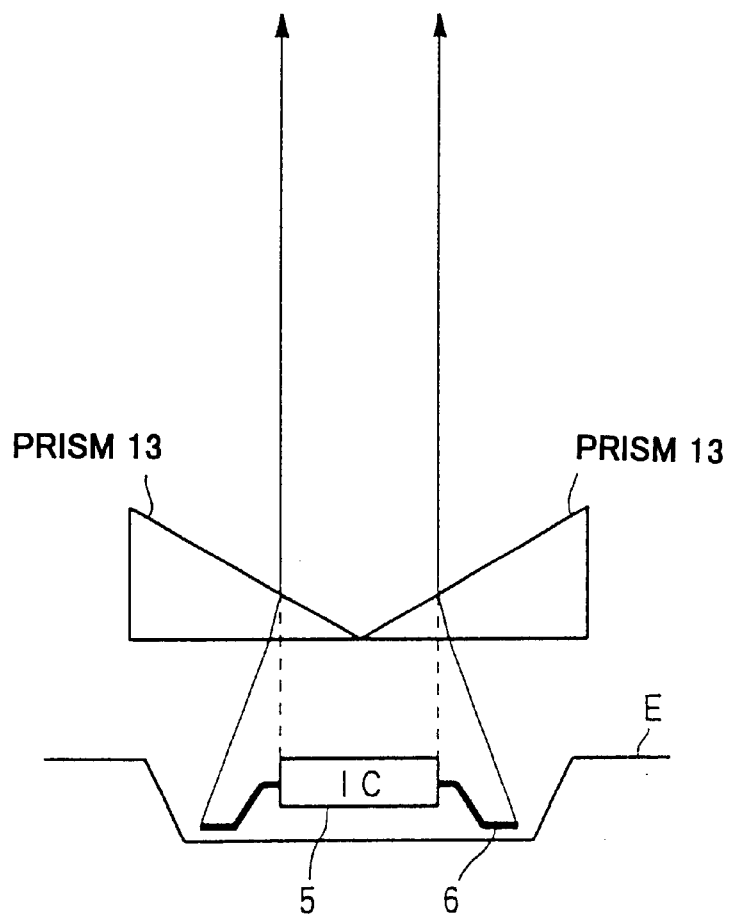

FIG. 8 shows a seventh embodiment of the present invention.

In this seventh embodiment as well, only an image of a SOP 5 lead portion is incident on a camera 1 via a prism 13, but in this case, from the standpoint of the figure, the right side lead portion image is incident on the field of view area of the right side of the camera 1, and the left side lead portion image is incident on the field of view area of the left side of the camera 1.

Figure 9:
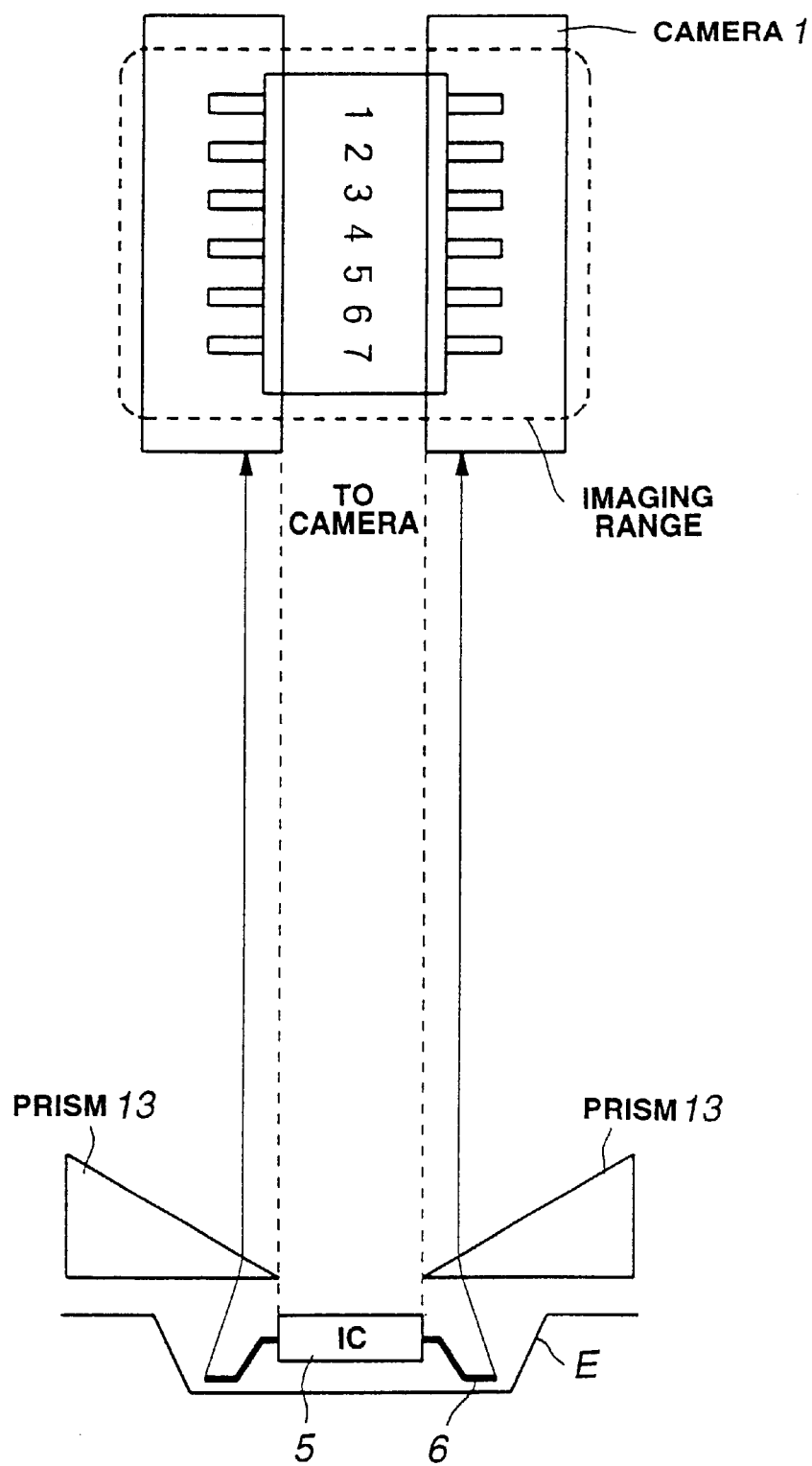
FIG. 9 is a diagram showing an eighth embodiment of the present invention.

FIG. 9 shows an eighth embodiment of the present invention.

In this eighth embodiment, a space is provided between the 2 prisms 13 of the seventh embodiment shown in FIG. 8, and a SOP 5 upper surface image is incident on a camera 1 via the gap thereof.

Further, in this case, the thickness and refractive index of the prism 13 is set on the basis of the above equation (1), and it is possible to bring the SOP upper surface image and lead portion image into focus simultaneously.

Figure 10:
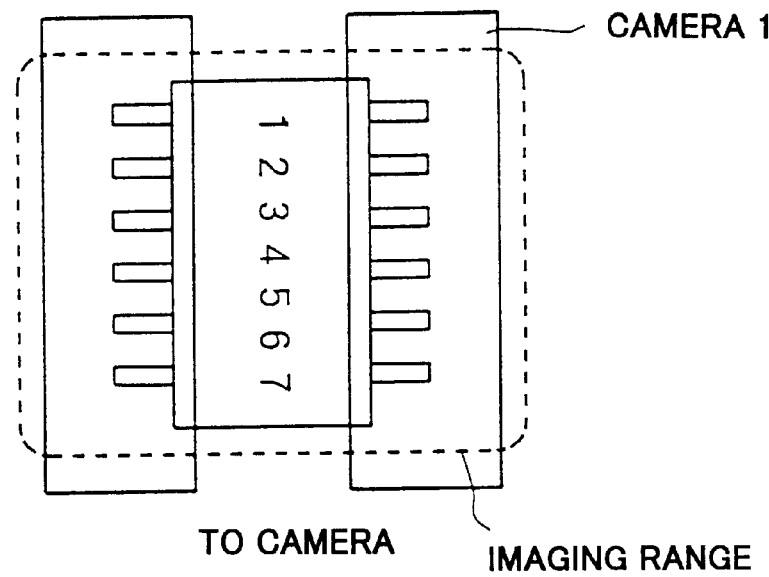
FIG. 10 is a diagram showing a ninth embodiment of the present invention.
Figure 10:
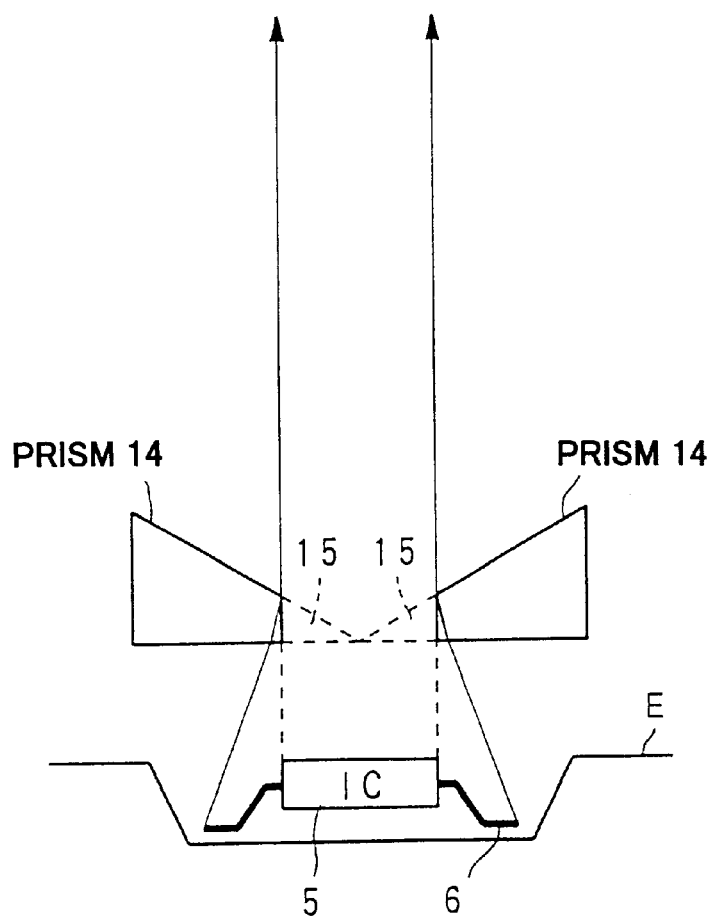

FIG. 10 shows a ninth embodiment of the present invention.

In this ninth embodiment, a portion 15 of the 2 prisms 14 located above the upper surface of a SOP 5 has been omitted, thereby preventing these prisms 14 from interfering with the image of the upper surface of the SOP 5.

In this embodiment as well, the thickness and refractive index of a prism 14 is set on the basis of the above equation (1), and it is possible to bring the SOP upper surface image and lead portion image into focus simultaneously.

Furthermore, nothing in particular was mentioned with regard to lighting in any of the above-described embodiments, but since wavelength dispersion occurs and becomes the cause of false data when using a prism as in the embodiments shown in FIG. 2, and FIG. 6 through FIG. 10, it is desirable to use a monochromatic light source as lighting.

A tenth embodiment is constituted to solve for troubles when a SOP 5 shifts from the IC housing portion EA within an embossed tape E.

That is, as shown in FIG. 11(c), when an attempt is made to image a SOP 5 lead 6 with a camera from directly above, if the SOP 5 shifts from the IC housing area EA within the embossed tape E as shown in FIG. 11(a), as shown in FIG. 11(a) (b), a reflected image of the lead 6 appears on the side wall EG of the embossed tape E, not only the lead image, but the image of the lead reflected by the side wall is also incident on the camera as shown in FIG. 11(c). As a result thereof, in a case like this, lead measurement accuracy is impaired, inspection becomes impossible, and other such trouble occurs.

Accordingly, in this tenth embodiment, in addition to P polarizing the lighting relative to the SOP 5 lead portion, the imaging direction of the camera is made to correspond to the vicinity of the Brewster angle φB (Brewster angle ±20°) relative to the side wall of the embossed tape E.

Figure 12:
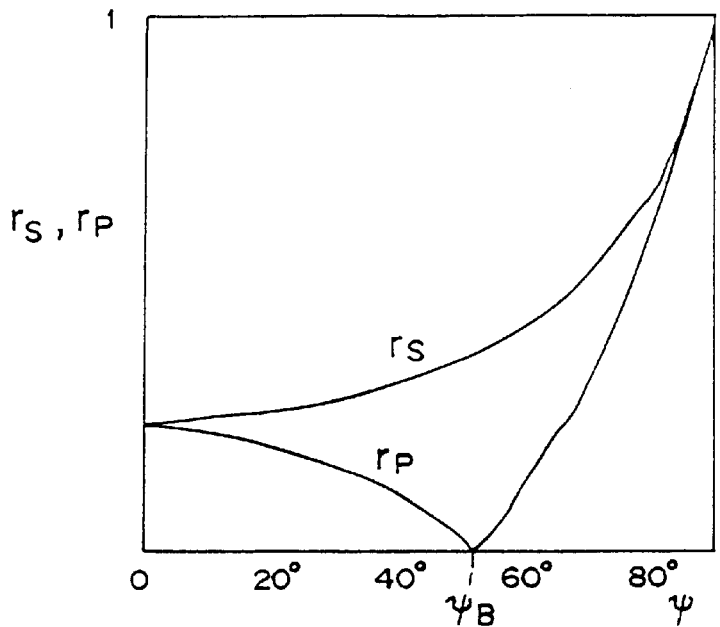
FIG. 12 is a diagram showing the reflection coefficient of the P, S polarized waves of embossed tape.

That is, if the amplitude reflection coefficient γ relative to the angle of incidence φ at the surface of the embossed tape E is found for a P polarized wave (γp) and an S polarized wave (γs), respectively, the results are as shown in FIG. 12.

In accordance with the reflection characteristics shown in this FIG. 12, when the angle of incidence φ relative to the embossed tape is in the vicinity of the Brewster angle (ordinarily 50°–60°), P polarization reflection becomes zero.

Figure 13:
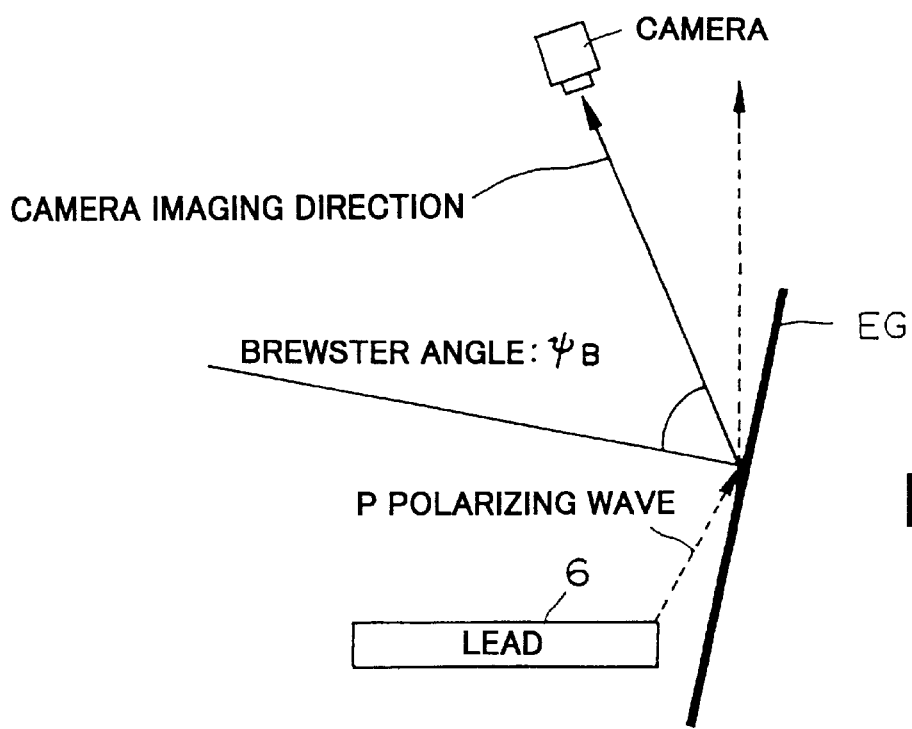
FIG. 13 is a diagram showing a tenth embodiment of the present invention.

Therefore, as shown in FIG. 13, if, in addition to P polarizing the lighting for imaging a SOP 5 lead portion, the imaging direction of the camera is made to correspond to a proximate Brewster angle φB relative to the side wall of the embossed tape E, the reflected light from the embossed tape side wall EG is not reflected on the camera, making it possible to solve for the above-described troubles.

Figure 14:
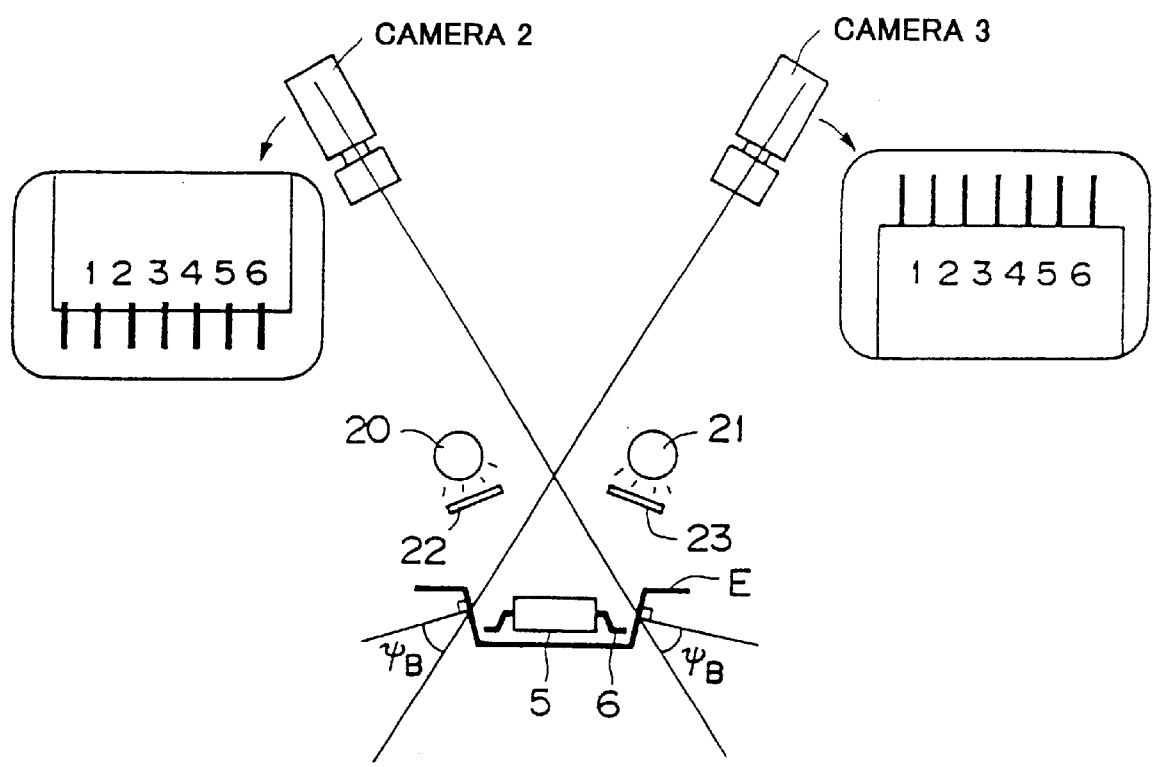
FIG. 14 is a diagram showing a eleventh embodiment of the present invention.

FIG. 14 shows an eleventh embodiment of the present invention.

This eleventh embodiment embodies the tenth embodiment shown in the above FIG. 13, and provides 2 cameras 2, 3 to image both the right and left lead portions, respectively. That is, camera 2 images the lead portion on the right side of the figure, and camera 3 images the lead portion on the left side. Here, the imaging direction of each camera 2, 3 is made to correspond to a proximate Brewster angle φB relative to the side wall of the embossed tape E.

Further, as illumination for the lead portion, lights 20, 21, and polarizing plates 22, 23, which P polarize the illumination of each light, are provided. Furthermore, the type and location of the lights 20, 21 is optional so long as they are capable of suitably illuminating the lead portions.

Figure 15:
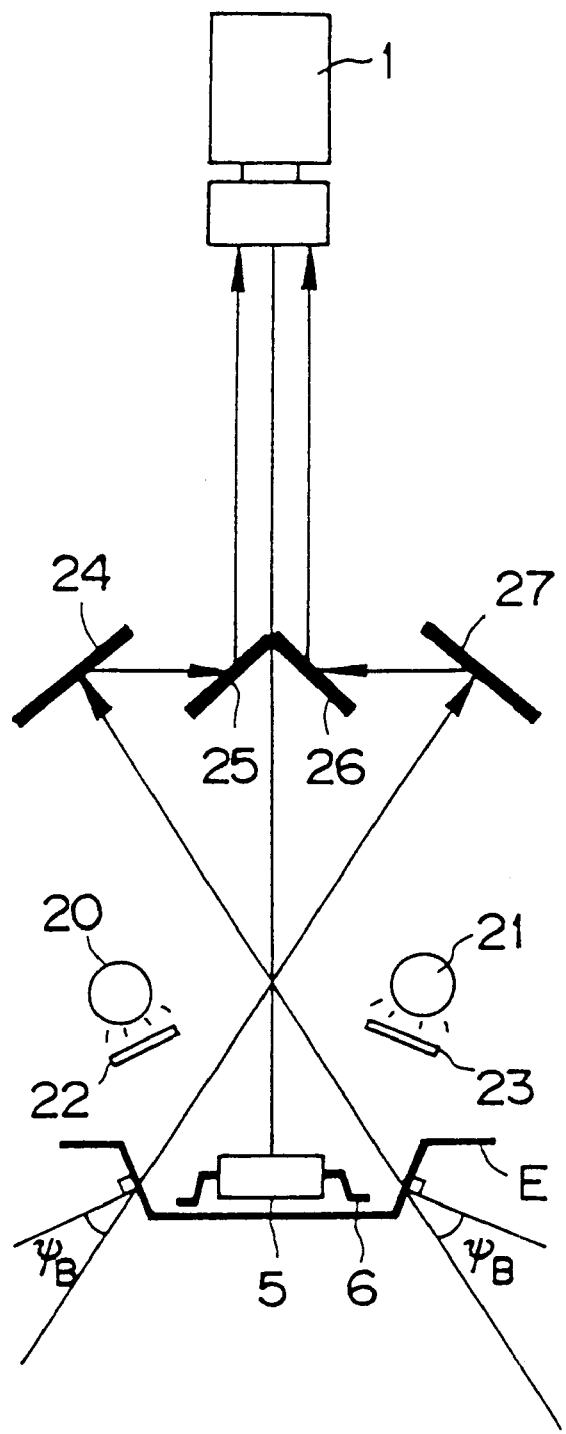
FIG. 15 is a diagram showing a twelfth embodiment of the present invention.

FIG. 15 shows a twelfth embodiment of the present invention.

In this twelfth embodiment, 4 mirrors 24–27 are provided for imaging both the right and left lead portions of a SOP 5 using 1 camera 1. In this case as well, the configuration locations and configuration angles of the mirrors 24–27 are set so that the imaging direction of the camera 1 relative to the right and left lead portions constitutes a proximate Brewster angle φB relative to the side wall of the embossed tape E. Further, as illumination for the lead portions, lights 20, 21, and polarizing plates 22, 23, which P polarizes the illumination of each light, are provided the same as described above.

Figure 16:
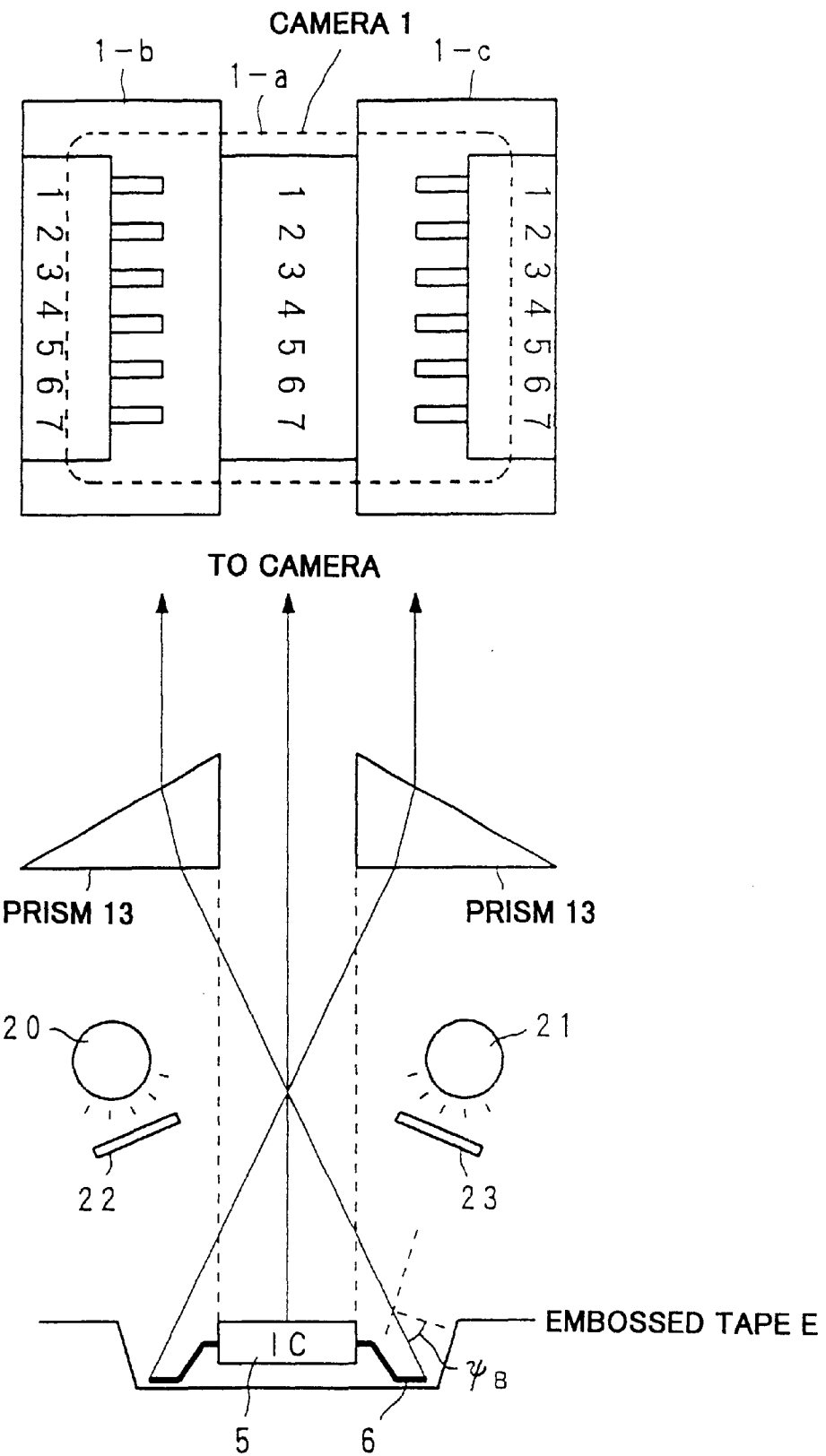
FIG. 16 is a diagram showing a thirteenth embodiment of the present invention.

FIG. 16 shows a thirteenth embodiment of the present invention.

This thirteenth embodiment adds to the above fifth embodiment shown in FIG. 6 the above-described configuration for preventing embossed tape reflecting light, a prism 13 is set so that the camera 1 imaging direction related to the side portion regions 1-b, 1-c of the field of view area of this camera 1 corresponds to a proximate Brewster angle φB relative to the side wall of the embossed tape E, and as illumination for the lead portions, lights 20, 21, and polarizing plates 22, 23, which P polarizes the illumination of each light, are provided.

Figure 17:
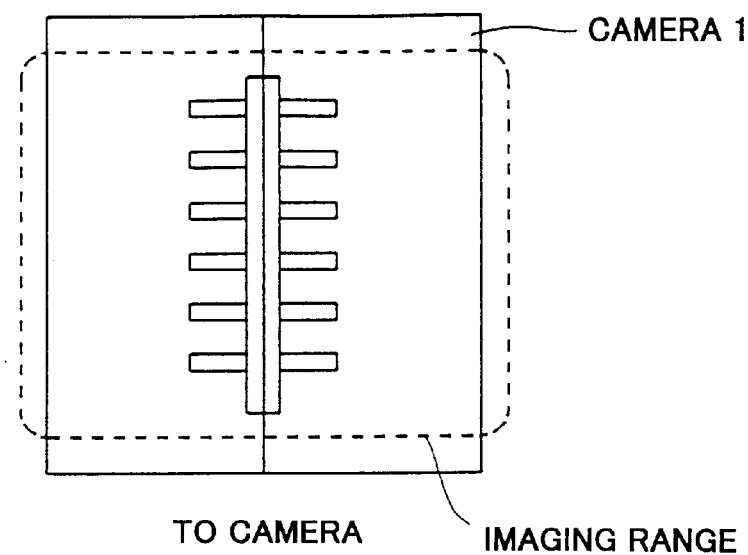
FIG. 17 is a diagram showing a fourteenth embodiment of the present invention.
Figure 17:
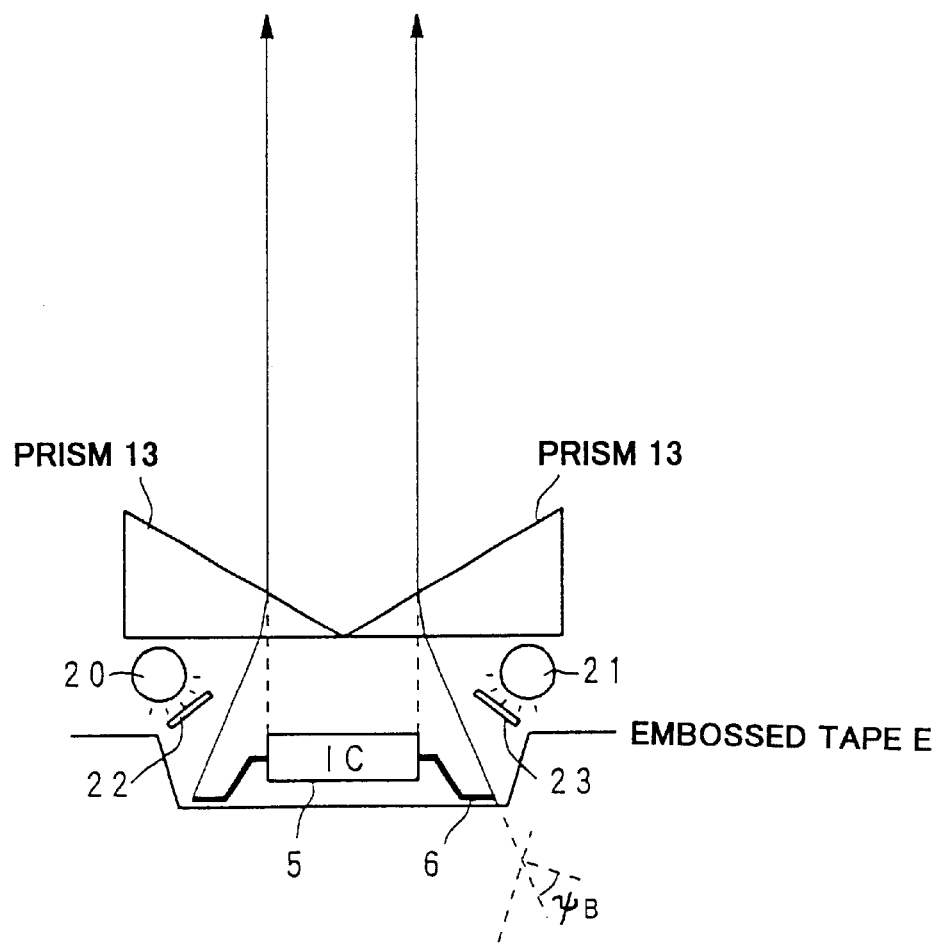

FIG. 17 shows a fourteenth embodiment of the present invention.

This fourteenth embodiment adds to the above seventh embodiment shown in FIG. 8 the above-described configuration for preventing embossed tape reflecting light, a prism 13 is thus set so that the camera 1 imaging direction corresponds to a proximate Brewster angle φB relative to the side wall of the embossed tape E, and as illumination for the lead portions, lights 20, 21, and polarizing plates 22, 23, which P polarizes the illumination of each light, are provided.

Figure 18:
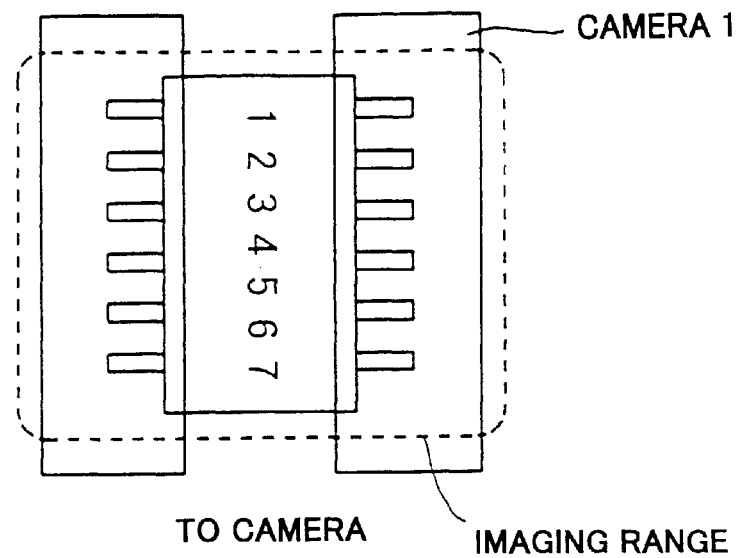
FIG. 18 is a diagram showing a fifteenth embodiment of the present invention.
Figure 18:
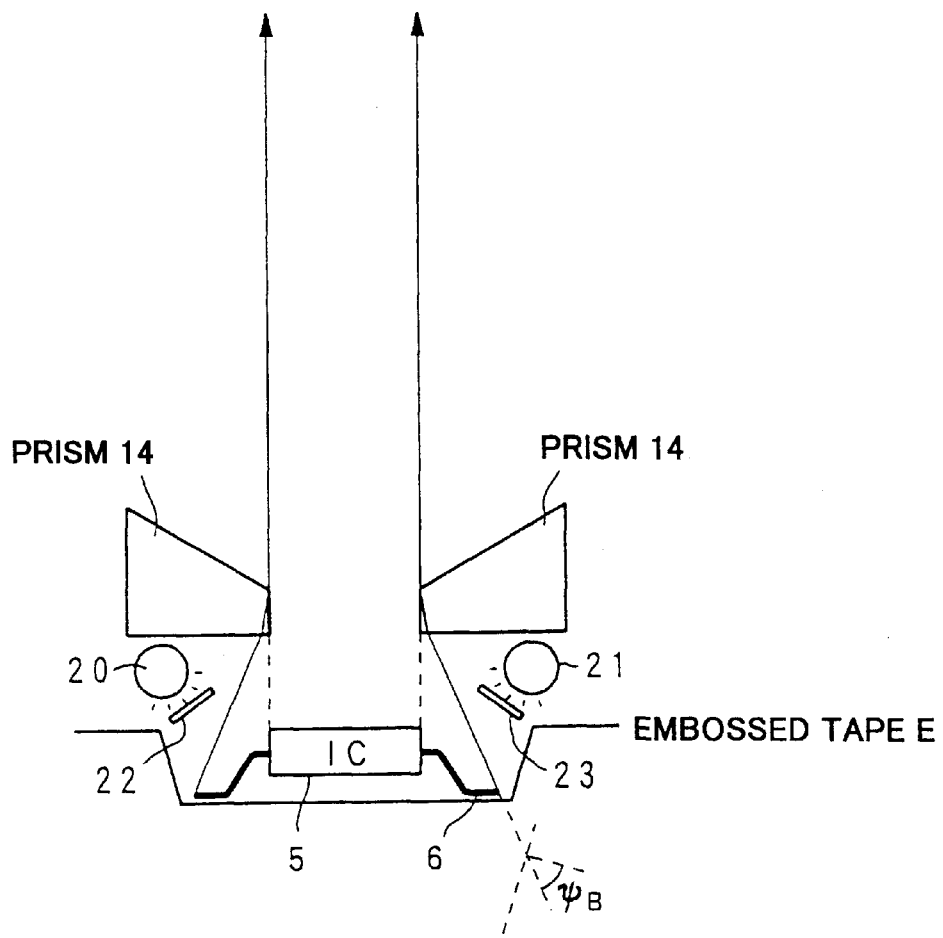

FIG. 18 shows a fifteenth embodiment of the present invention.

This fifteenth embodiment adds to the above ninth embodiment shown in FIG. 10 the above-described configuration for preventing embossed tape reflecting light, a prism 13 is thus set so that the camera 1 imaging direction corresponds to a proximate Brewster angle φB relative to the side wall of the embossed tape E, and as illumination for the lead portions, lights 20, 21, and polarizing plates 22, 23, which P polarizes the illumination of each light, are provided.

Figure 19:
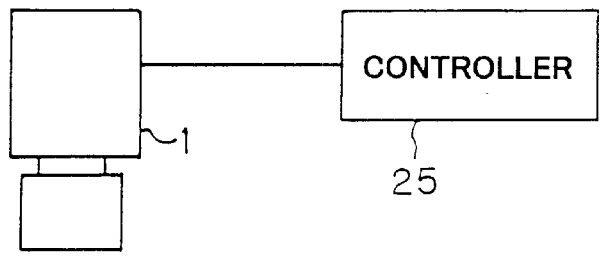
FIG. 19 is a diagram showing a sixteenth embodiment of the present invention.
Figure 19:
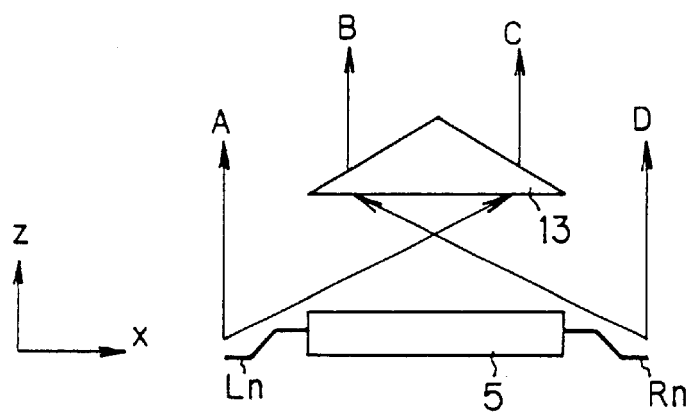

FIG. 19 shows a sixteenth embodiment of the present invention.

In this embodiment, a prism 13 is provided above a SOP 5, and a camera 1 is provided yet thereabove, enabling 1 camera 1 to image from 2 different directions an image of the tips of leads of the SOP 5 in accordance with the intervening of the prism 13 therebetween. That is, the image of the left lead Ln of the SOP 5 is incident on the camera 1 via optical path A, C, and the image of the right lead Rn is incident on the camera 1 via optical path B, D.

Figure 20A:
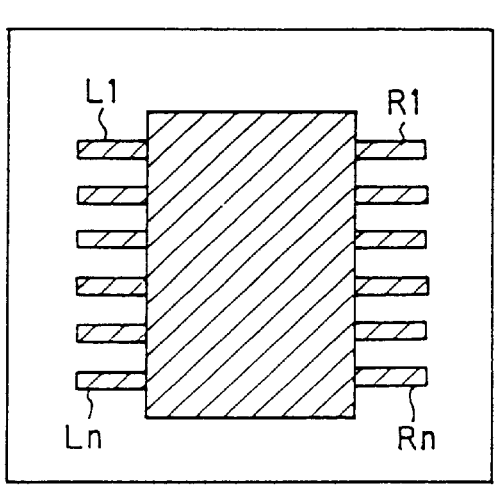
FIGS. 20(a) and 20(b) are diagrams showing examples of images in accordance with the sixteenth embodiment.
Figure 20B:
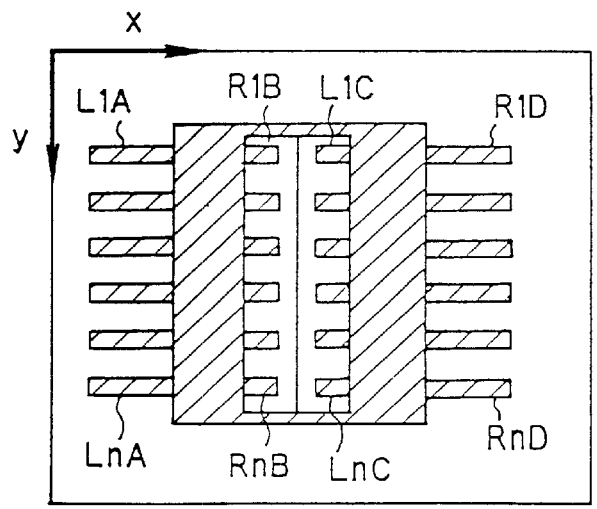

FIG. 20(a) is a plan view showing a SOP 5 from above, and the SOP 5 has left leads L1–Ln, and right leads R1–Rn. FIG. 20(b) shows the image of the SOP 5 shown in FIG. 20(a) imaged by a camera 1, and each lead L1–Ln and R1–Rn is reproduced by the camera 1 within 1 image as images L1A–LnA, L1C–LnC, and R1A–RnA, R1C–RnC, respectively, in 2 different x direction locations. For example, left lead L1 is reproduced by the camera 1 at 2 locations, L1A and L1C, within the image.

Furthermore, in this case, a lead image in accordance with optical path A, C, which does not go through the prism 13, and a lead image in accordance with optical path B, D, which does go through the prism 13 are incident on the camera 1, but the refractive index and thickness of the prism 13 is set so that the difference between the optical path lengths thereof can be absorbed.

Controlling portion 25 computes on the basis of the camera image the height location in the z direction of leads L1–Ln and R1–Rn using the triangulation principle. That is, since lead images L1A–LnA, L1C–LnC, and R1A–RnA, R1C–RnC, which image each lead L1–Ln, R1–Rn from 2 different directions, are reproduced by the camera 1, the x coordinates thereof can be used to find the z coordinates of each lead L1–Ln, R1–Rn. Of course, the x–y location of the tip of a lead can also be found using triangulation.

Figure 21:
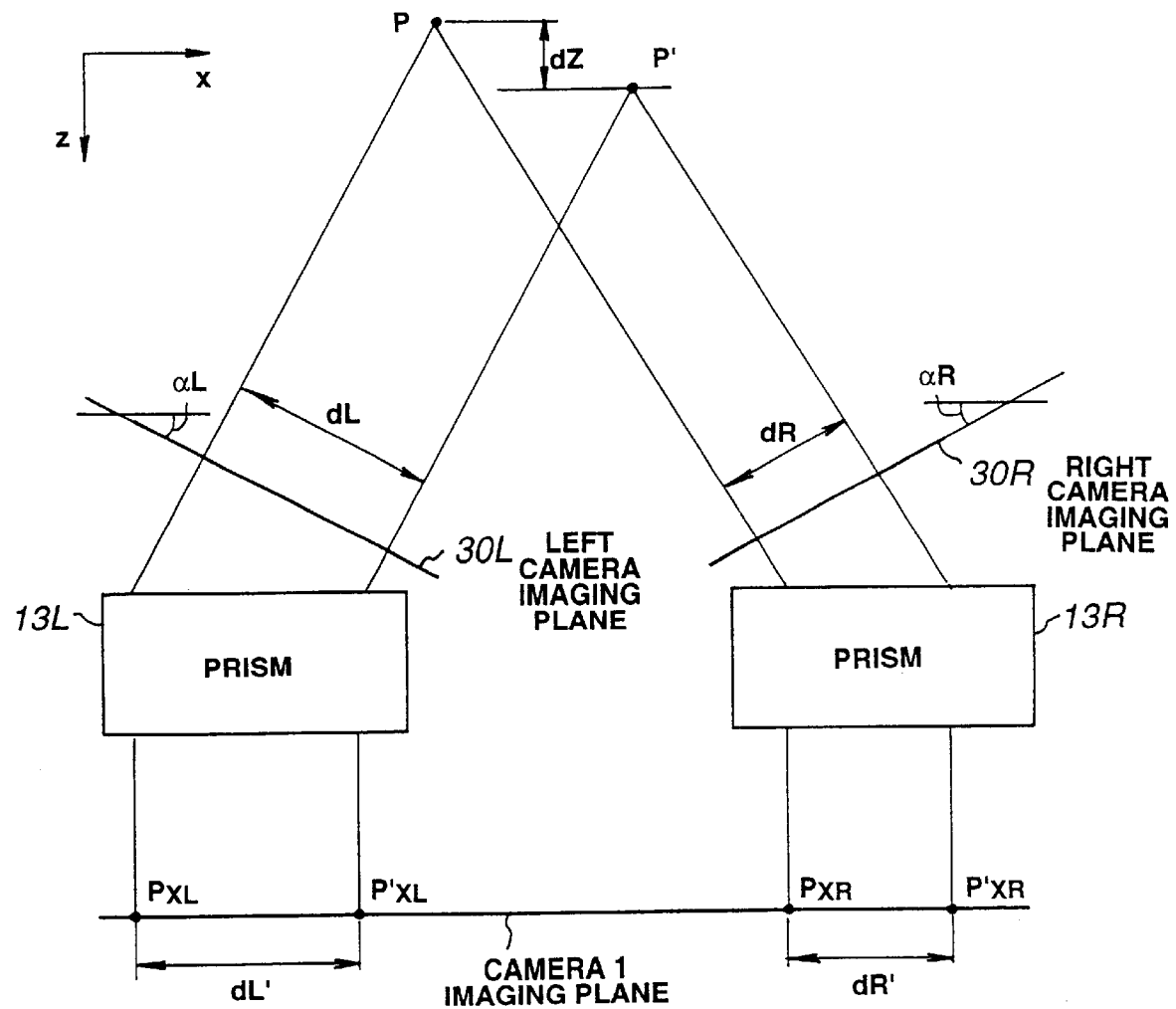
FIG. 21 is a diagram illustrating the lead height measurement principle in accordance with triangulation.

FIG. 21 is a diagram for explaining the basic principle for finding the z direction coordinate location of the tip of a lead using triangulation.

In FIG. 21, it is assumed that point P is the lead tip location of a normal installation state, point P' is the actual tip location of a certain lead, and dz is a displacement in the z direction between these points P and P'.

When imaging is performed using 2 virtual cameras, the extent of this z direction displacement dz appears as displacement dL, dR in the imaging plane 30L, 30R of each virtual camera, and displacement dz is expressed as a function of dL, Dr in accordance with geometric conditions as in the below equation.

$$dz = (dL \cos \alpha R - dR \cos \alpha L)/(\sin \alpha L \cos \alpha R + \sin \alpha R \cos \alpha L)$$

$\alpha L$: gradient angle of left camera imaging plane $\alpha R$: gradient angle of right camera imaging plane (2)

Here, by providing prisms 13L, 13R in front of the camera imaging plane, the extent of displacement dL, dR in the above-mentioned left-right virtual camera imaging planes appears as dL', dR' in the camera 1 imaging plane.

Further, the relation between dL', dR' and dL, dR is as shown below.

$$dL' = CL \cdot dL$$

$$dR' = Cr \cdot dR$$

CL, CR: Prism-specific coefficients determined by the shape and refractive index of the prism (3)

Figure 22:
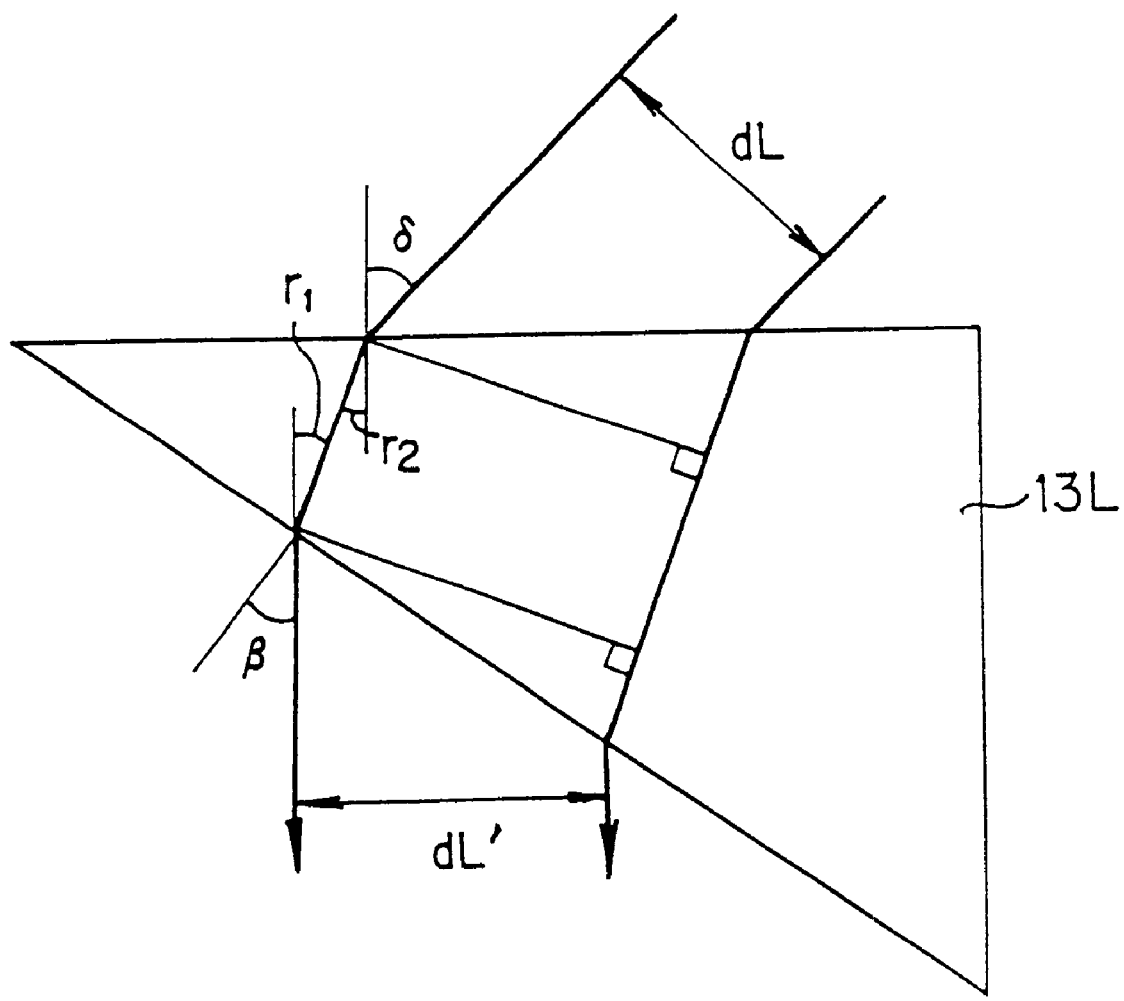
FIG. 22 is a diagram illustrating a prism-specific coefficient.

Furthermore, in the case of a prism like that shown in FIG. 22, the prism-specific coefficient CL is as shown below.

$$CL = (\cos \beta \cos \gamma 1)/(\cos \delta \cos \gamma 2) \quad (4)$$

Therefore, by finding beforehand on the camera 1 imaging plane the image locations PXL, PXR corresponding to a lead tip location P of a normal installation state, finding the deviations dL' and dR' between these locations PXL, PXR and image locations P'XL, P'XR corresponding to the actual lead tip location P', and substituting these deviations dL' and dR' in the above equation (2) and equation (3), makes it possible to find the height displacement dz relative to the normal state.

Furthermore, in the case of FIG. 21, the height displacement dz relative to the normal state of a lead tip was found, but it is also possible to specify the xyz coordinate locations in a three-dimensional space of lead tip location P' using the triangulation principle.

In this manner, in accordance with this sixteenth embodiment, since a prism 13 is disposed between a camera 1 and a SOP 5, and a lead image as seen from 2 different directions is incident on the camera 1, it is possible to obtain, in accordance with image data from only 1 camera provided above the SOP, data related not only to the xy location of a lead, but to the height direction location as well. In accordance therewith, a camera that images a SOP 5 directly from a diagonal direction can be omitted, and the system constitution can be made compact and inexpensive.

Further, in accordance with the prism, there are advantages over the method, which uses a mirror as in the above fourth embodiment shown in FIG. 5, such as compactness, no image reversal, no need for troublesome angle adjustments, and a high degree of freedom of deflection angle.

Figure 23:
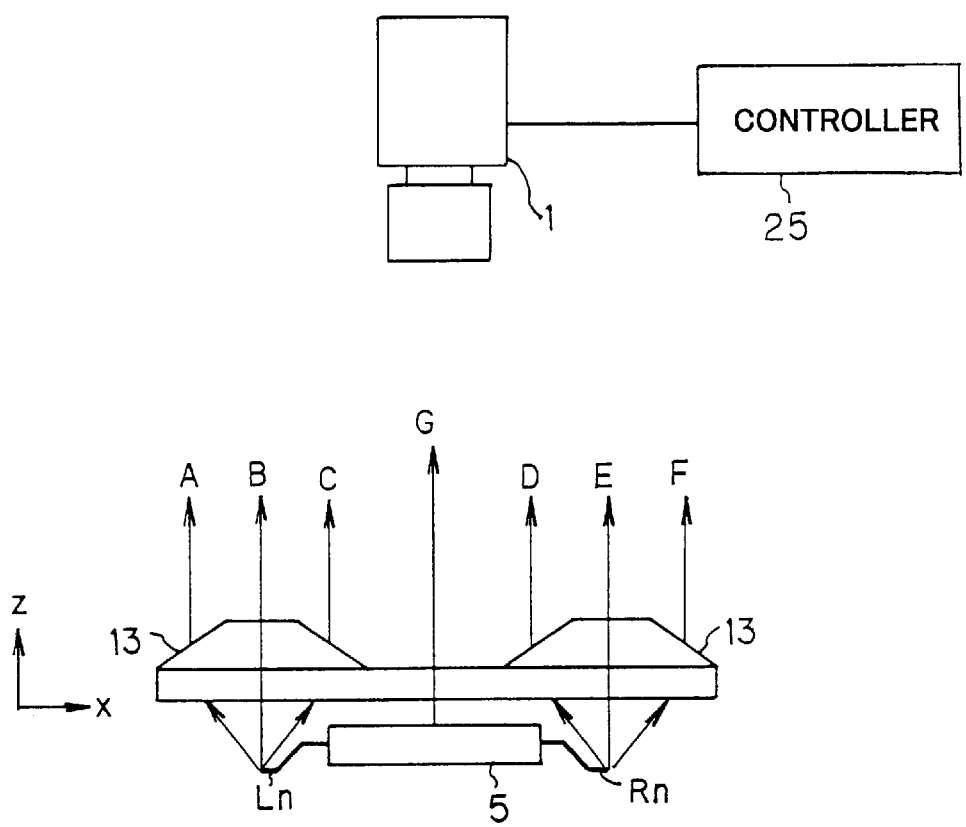
FIG. 23 is a diagram showing a seventeenth embodiment of the present invention.

FIG. 23 shows a seventeenth embodiment of the present invention.

In this embodiment, 2 doped prisms 13 are provided above a SOP 5, and a camera 1 is provided thereabove. In accordance with the intervening of 2 prisms 13, it is possible to image the lead tip image of the SOP 5 from 3 different directions using 1 camera 1. That is, an image of the left lead Ln of the SOP 5 is incident on the camera 1 via optical paths A, B, C, and an image of the right lead Rn is incident on the camera 1 via optical paths D, E, F.

Further, in this case, a space corresponding to the width of the SOP 5 upper surface portion is provided between the 2 doped prisms 13, and a SOP 5 upper surface image is directly incident on the camera 1 without going through the prisms 13, enabling a stamped marking inspection and a coplanarity inspection to be performed simultaneously with 1 camera 1.

Figures 24A, 24B:
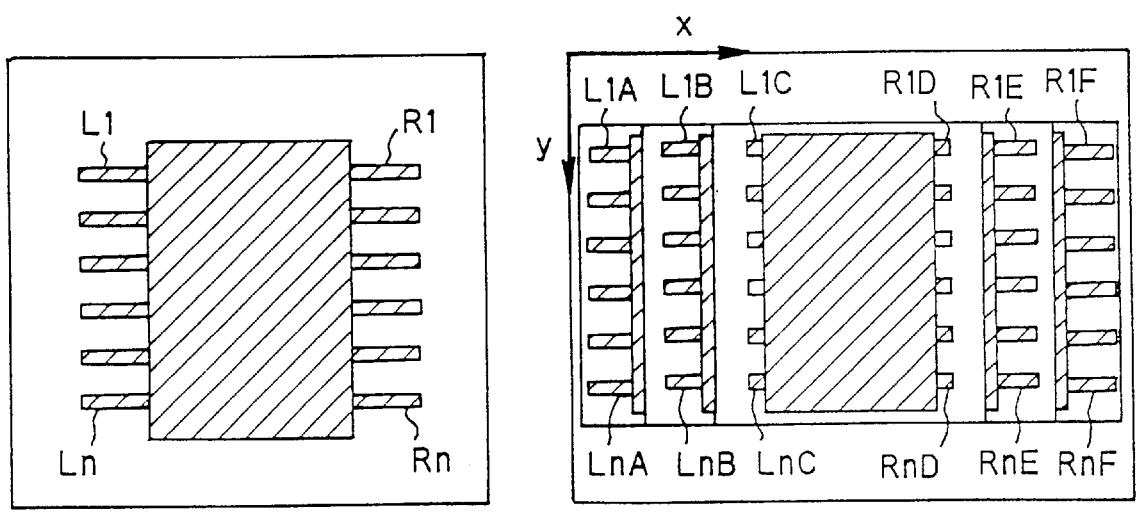
FIGS. 24(a) and 24(b) are diagrams showing examples of images in accordance with the seventeenth embodiment.

FIG. 24(a) is a plan view from above a SOP 5, having left leads L1–Ln, and right leads R1–Rn. FIG. 24(b) shows the image of the SOP 5 shown in FIG. 24(a) imaged in accordance with the camera 1 of FIG. 23, and the left leads L1–Ln are imaged in 3 different locations L1A–LnA, L1B–LnB, L1C–LnC within one image in accordance with the camera 1, and the right leads R1–Rn are imaged in 3 different xy locations R1D–RnD, R1E–RnE, R1F–RnF. For example, lead L1 is imaged from the perspective of 3 locations, L1A, L1B, L1C. Further, the SOP upper surface image is imaged in the center portion of the field of view of the camera 1.

Therefore, in this case, a controlling portion 25 can find the x coordinate displacement of a lead tip at 2 locations out of the 3 location lead tip images imaged within the camera 1 image, and can find the z coordinate of a lead tip using the above-mentioned triangulation principle.

Furthermore, in this embodiment as well, a SOP upper surface image in accordance with optical path G, which does not pass through a prism 13, and a lead image in accordance with optical paths A–F, which do pass through a prism 13, are incident on the camera 1, and the refractive index and thickness of the prisms 13 are set so that the difference in the optical path lengths thereof can be absorbed.

Figure 25:
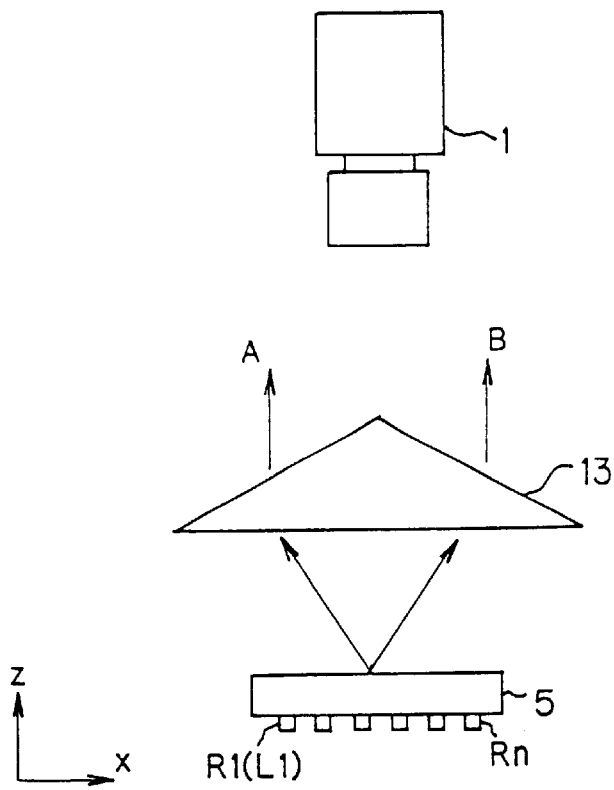
FIG. 25 is a diagram showing an eighteenth embodiment of the present invention.

FIG. 25 shows an eighteenth embodiment of the present invention.

In this eighteenth embodiment, the configuration angle of the SOP 5 of the above sixteenth embodiment shown in FIG. 19 is rotated 90 degrees. Therefore, when the SOP 5 is viewed from above as shown in FIG. 26(a), the left leads L1–Ln appear at the top, and the right leads R1–Rn appear at the bottom.

In this embodiment as well, the fact that a SOP 5 lead tip image can be imaged from 2 different direction using 1 camera 1 in accordance with the intervening of a prism 13 is the same as the above embodiment shown in FIG. 19. That is, an image of each lead L1–Ln, R1–Rn of SOP 5 is incident on the camera 1 via 2 types of optical paths A, B.

Figure 26A:
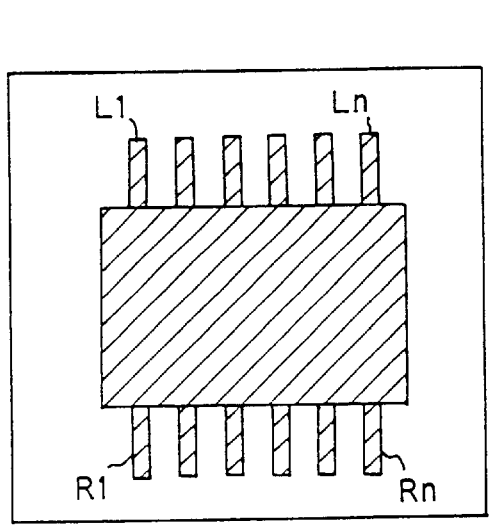
FIGS. 26(a) and 26(b) are diagrams showing examples of images in accordance with the eighteenth embodiment.
Figure 26B:
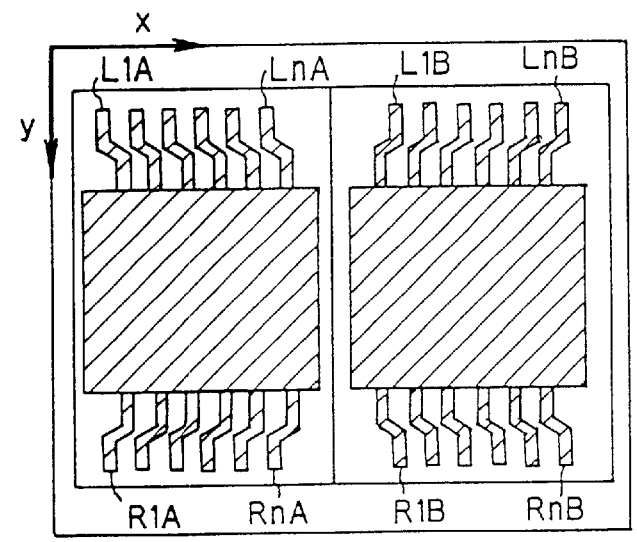

FIG. 26(b) shows an image of the SOP 5 shown in FIG. 26(a) imaged by the camera 1 of FIG. 25, and the left leads L1–Ln are imaged as images L1A–LnA, L1B–LnB, which are located in 2 different locations within one image in accordance with the camera 1, and the right leads R1–Rn are imaged as lead images R1C–RnC, R1D–RnD, which are located in 2 different locations. For example, lead L1 is imaged from the standpoints of 2 locations, L1A, L1B.

Therefore, in this case as well, the image data of 1 camera 1 can be used to find the z coordinate of a lead tip based on the above-described triangulation principle.

Figure 27:
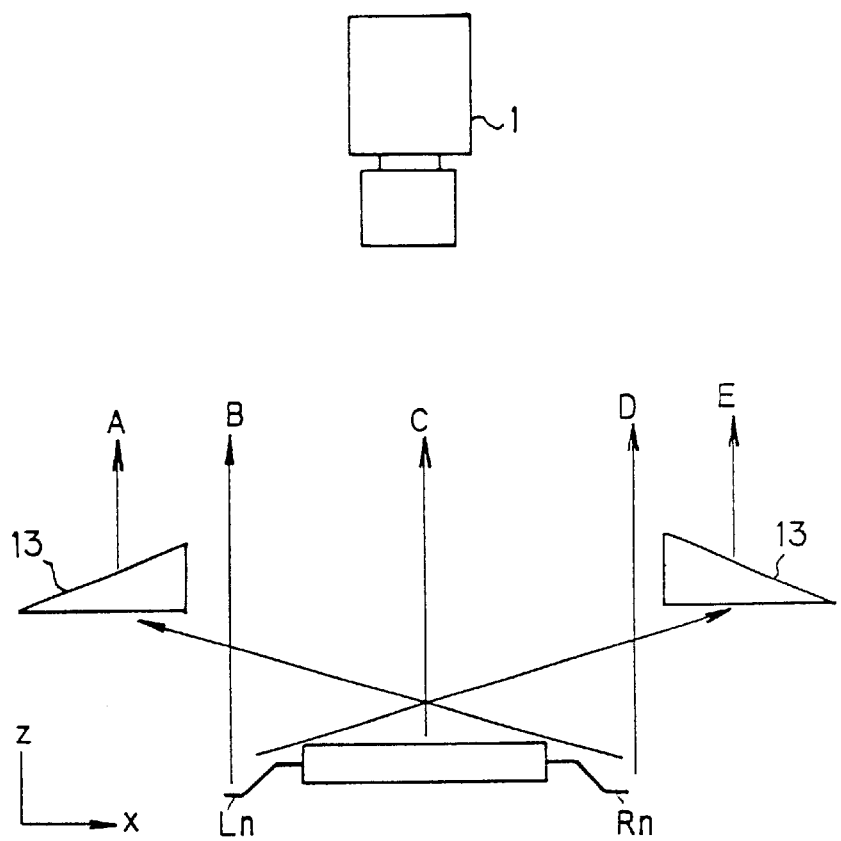
FIG. 27 is a diagram showing a nineteenth embodiment of the present invention.
Figures 28A, 28B:
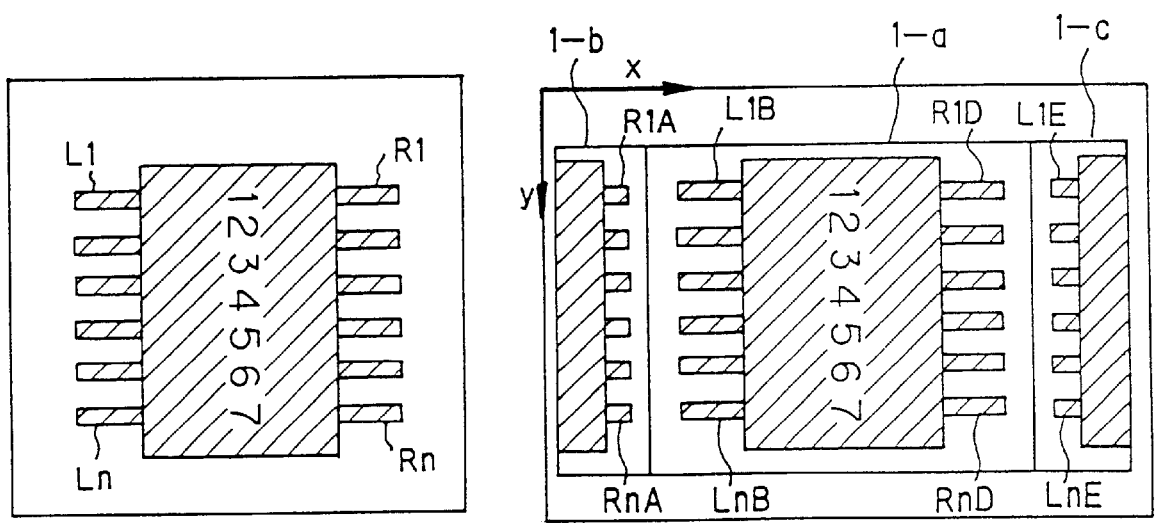
FIGS. 28(a) and 28(b) are diagrams showing examples of images in accordance with the nineteenth embodiment.

FIG. 27 shows a nineteenth embodiment of the present invention.

In this nineteenth embodiment, a SOP upper surface stamped markings inspection and lead coplanarity inspection are performed using 1 CCD camera 1 similar to the above fourth embodiment shown in FIG. 5, the fifth embodiment shown in FIG. 6, and the seventeenth embodiment shown in FIG. 23.

In this case, the gap between the 2 prisms 13 is widened so that a SOP 5 upper surface image, to include a lead image, can be imaged in the center region 1-a of the field of view area of the camera 1 from directly overhead, and so that the SOP 5 lead portion 6 can be imaged at a predetermined angle in the edge regions 1-b, 1-c of the field of view area of the camera 1. In this case, the camera 1 imaging axis is deflected by the prisms 13 so that the image of the right leads R1–Rn is incident on the left edge region 1-b of the field of view area of the camera 1, and the image of the left leads L1–Ln is incident on the right edge region 1-c of the field of view area of the camera 1.

Furthermore, in this embodiment as well, a SOP upper surface image in accordance with optical paths B, C, D, which do not pass through a prism 13, and a lead image in accordance with optical paths A, E, which do pass through a prism 13, are incident on the camera 1, and the refractive index and thickness of the prisms 13 are set so that the difference in the optical path lengths thereof can be absorbed.

Figure 29:
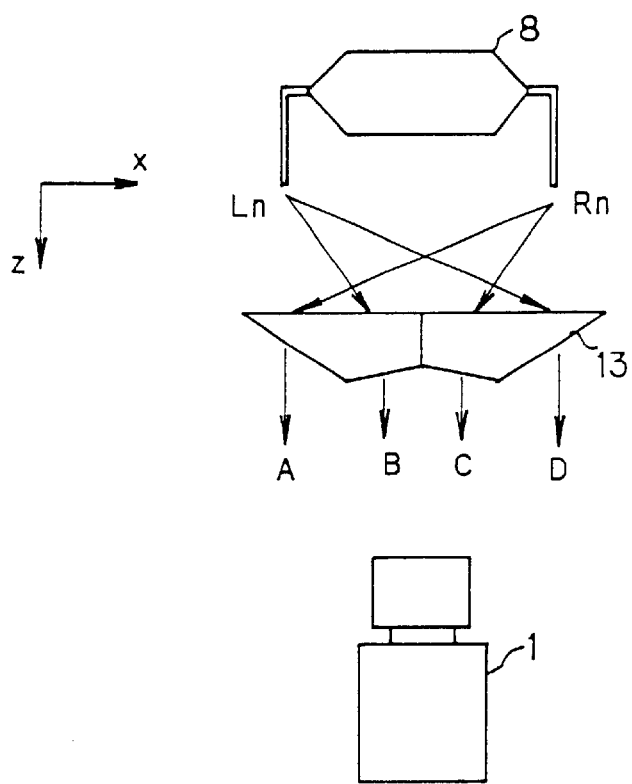
FIG. 29 is a diagram showing a twentieth embodiment of the present invention.

FIG. 29 shows a twentieth embodiment of the present invention.

This twentieth embodiment measures the coplanarity of each lead tip of a DIP (Dual Inline Package) 8.

In this case, a camera 1 is provided to enable the imaging of the back surface side of the DIP 8, and a prism 13 is provided between the camera 1 and the DIP 8.

Figure 30A:
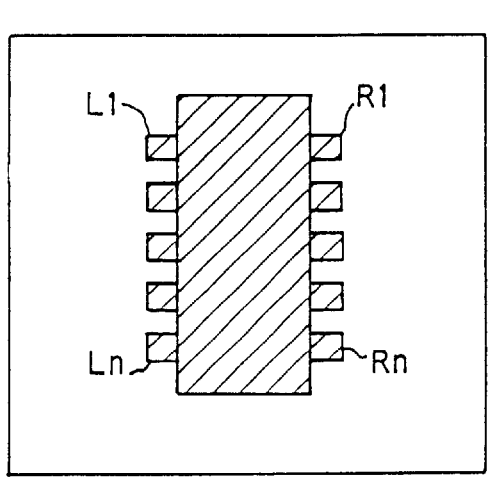
FIGS. 30(a) and 30(b) are diagrams showing examples of images in accordance with the twentieth embodiment.
Figure 30B:
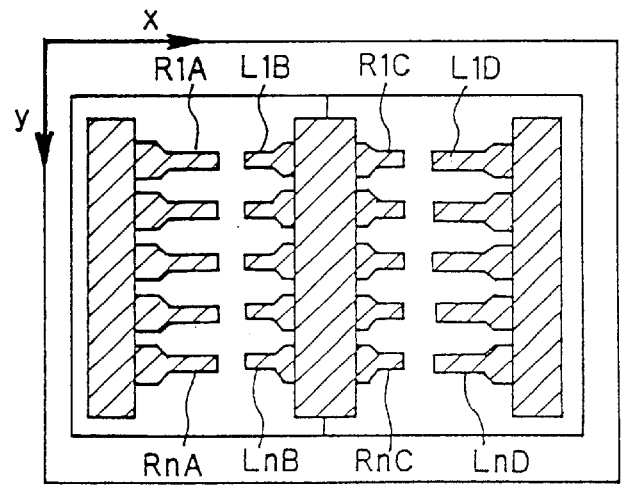

FIG. 30(a) is a plan view of a DIP 8 viewed from above, and the DIP 8 has left leads L1–Ln and right leads R1–Rn. FIG. 30(b) shows an image of the DIP 8 shown in FIG. 30(a) imaged by the camera 1 of FIG. 29, and the left leads L1–Ln are imaged in 2 different locations, L1B–LnB, L1D–LnD, within one image in accordance with the camera 1, and the right leads R1–Rn are imaged in 2 different locations, R1A–RnA, R1C–RnC.

In this embodiment as well, since a prism 13 is disposed between the camera 1 and a DIP 8, and lead images viewed from 2 different directions are incident on the camera 1, it is possible to obtain, in accordance with image data from only 1 camera provided above the SOP, data related not only to the xy location of a lead, but to the height direction location as well.

Figure 31:
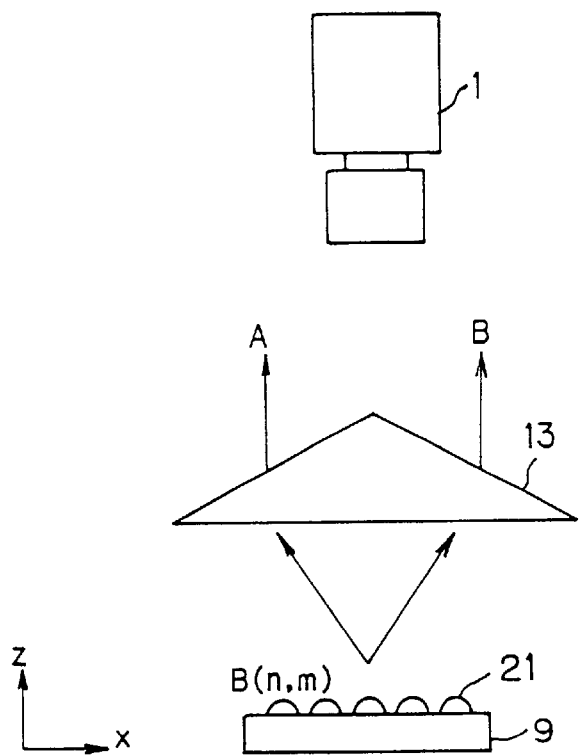
FIG. 31 is a diagram showing a twenty-first embodiment of the present invention.

FIG. 31 shows a twenty-first embodiment of the present invention.

This twenty-first embodiment of the present invention measures the coplanarity of each ball-shaped lead 21 of a BGA (Ball Grid Array) 9 or CSP (Chip Size Package).

In this case, a camera 1 is provided above a BGA 9, which has been turned upside-down, and a prism 13 is provided between the camera 1 and the BGA 9.

Figures 32A, 32B:
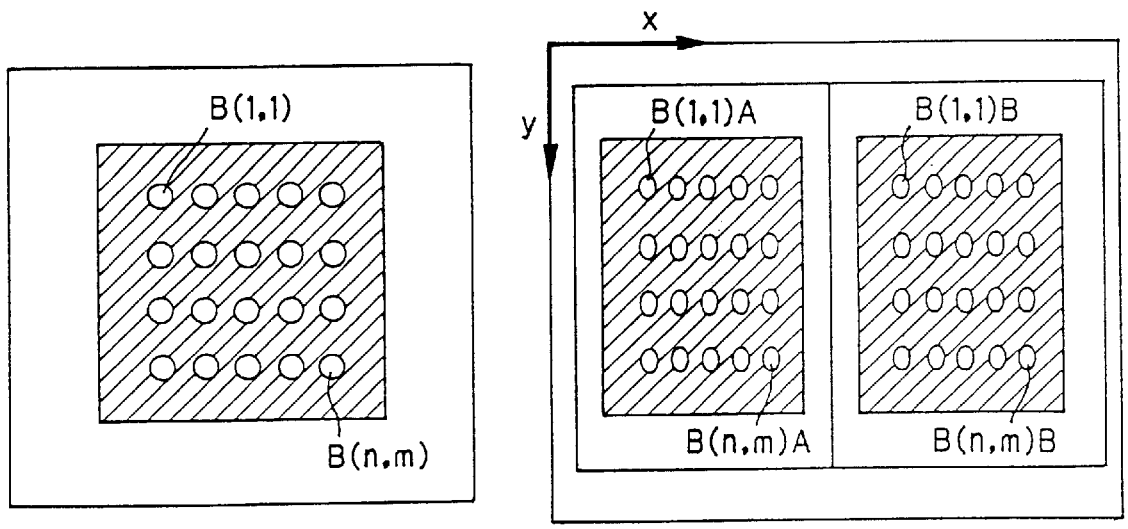
FIGS. 32(a) and 32(b) are diagrams showing examples of images in accordance with the twenty-first embodiment.
Figure 33:
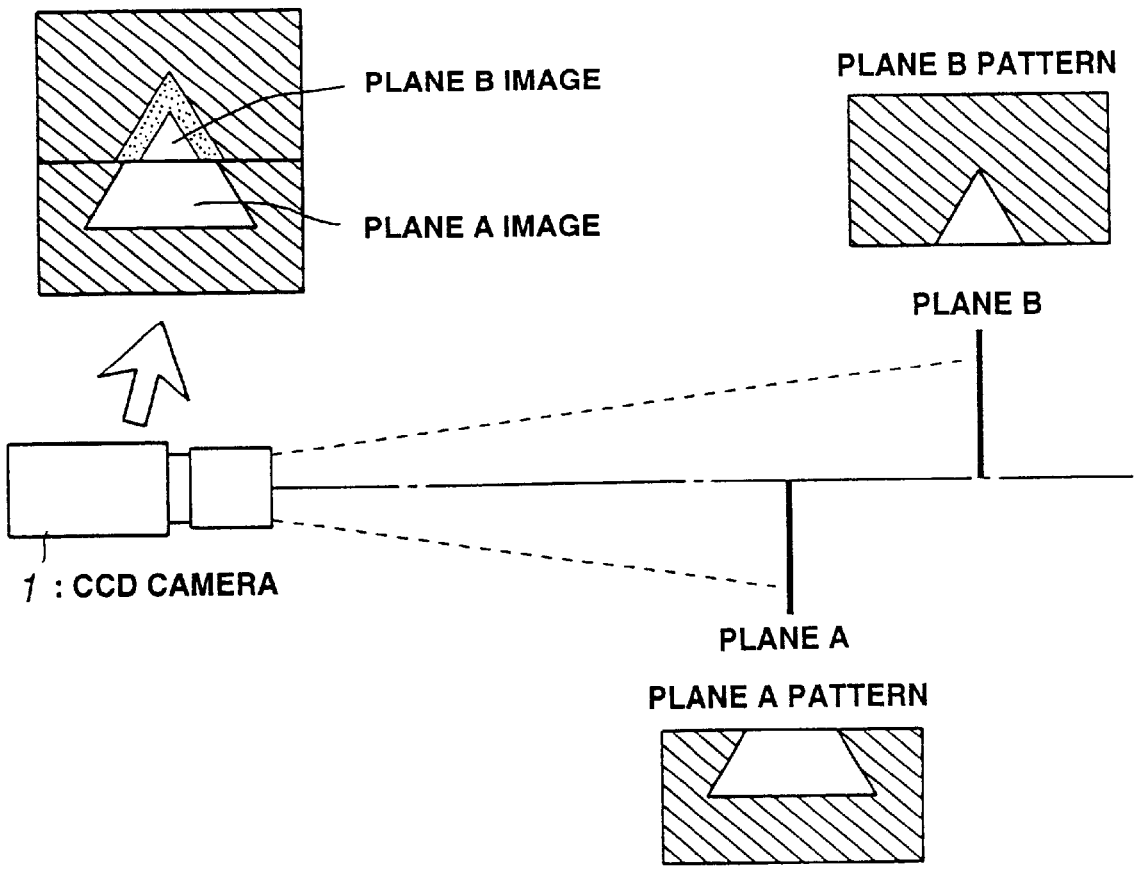
FIG. 33 is a diagram showing prior art.
Figure 34:
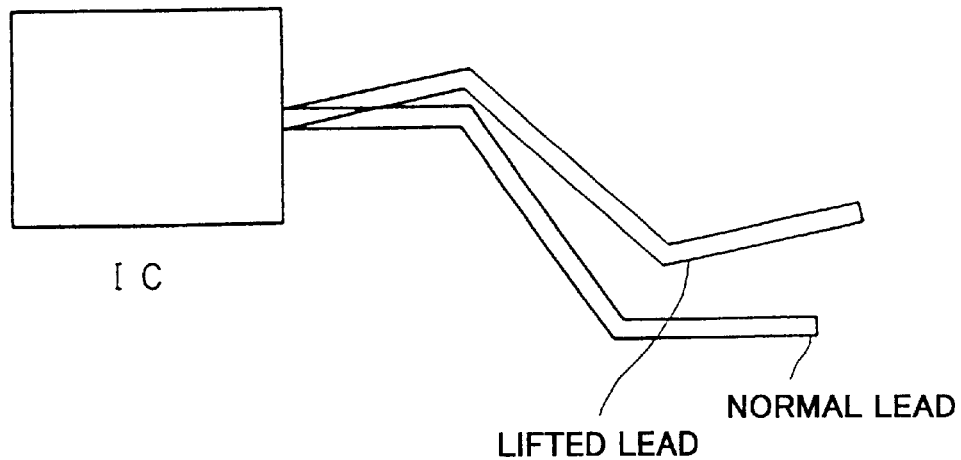
FIG. 34 is a diagram showing the object of a lead coplanarity inspection.
Figure 35A:
FIGS. 35(a) and 35(b) are diagrams showing prior art.
Figure 35B:
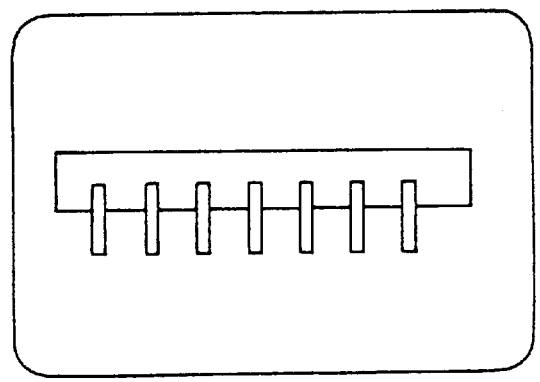
Figure 36A:
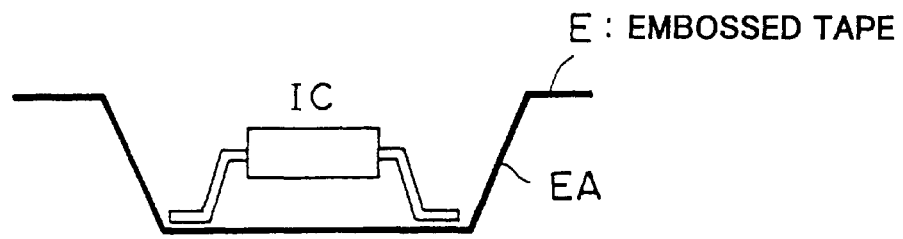
FIGS. 36(a) and 36(b) are diagrams showing IC packages housed inside embossed tape.
Figure 36B:
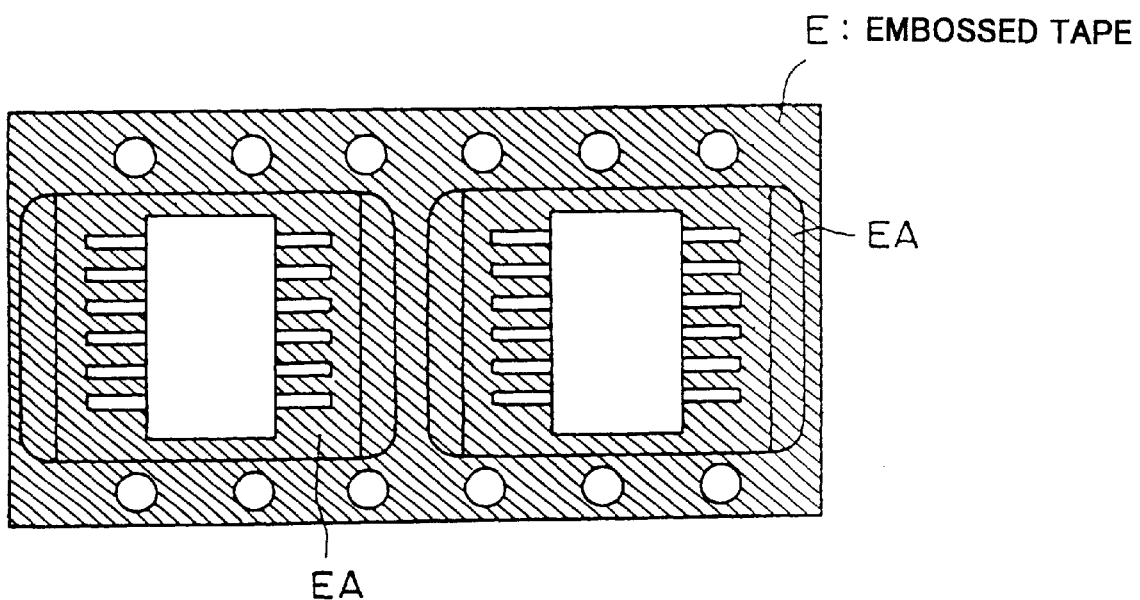

FIG. 32(a) is a plan view of a BGA 9 viewed from above, and the BGA 9 has ball-shaped leads B(1,1)-B(n,m) arrayed vertically and horizontally. FIG. 32(b) shows an image of the BGA 9 shown in FIG. 32(a) imaged by the camera 1 of FIG. 31, and, in accordance with the intervening of a prism 13, the ball-shaped leads B(1,1)-B(n,m) are imaged within 1 image in accordance with the camera 1 as images B(1,1)A-B(n,m)A, B(1,1)B—B(n,m)B, which are 2 different right-left locations.

In this embodiment as well, since a prism 13 is disposed between the camera 1 and a BGA 9, and ball-shaped lead images viewed from 2 different directions are incident on the camera 1, it is possible to obtain, in accordance with image data from only 1 camera provided above the BGA 9, data related not only to the xy location of a lead, but to the height direction location as well.

Now then, in the above-mentioned embodiments, the present invention was applied to SOP, DIP, BGA, but the present invention can also be applied to lead inspections of arbitrary other semiconductor packages, such as PGA (Pin Grid Array), QFP (Quad Flat Package), QFJ (Quad Flat J-leaded Package) and the like. Further, the present invention can also be applied to the inspection of arrays of connectors and other electrodes. Further, the present invention can also be applied to bonding wire height inspections.

Furthermore, the present invention can also be applied to a coplanarity inspection of a state in which a leadframe is hanging down prior to breaking off.

Industrial Applicability

When using 1 imaging means to image a plurality of objects to be inspected, for which the optical path lengths to the imaging means differ, focusing can be performed simultaneously for all the objects to be inspected, the time required for imaging can be shortened, and a high quality image can be obtained over the entire region of the imaged area.

What is claimed is:

1. An inspection object imaging device, which images an upper surface and a side surface of an object to be inspected with one imaging means provided above the object to be inspected, characterized in that a light transmitting prism mirror having a predetermined refractive index is provided to the side of the object to be inspected, and a thickness of the prism mirror is set to a value, which absorbs an optical path length difference between an optical path from the upper surface of the object to be inspected to the imaging means, and an optical path from the side of the objects to be inspected via the prism mirror to the imaging means.

2. A semiconductor package inspection device, which inspects a coplanarity of leads of a semiconductor package housed in a predetermined container, characterized in that the semiconductor package inspection devices comprises:

lighting means for illuminating with a P polarizing wave a lead portion of the semiconductor package;

imaging means for imaging the lead portion of the semiconductor package from diagonally above at a predetermined angle, an imaging direction thereof being set at a Brewster angle relative to a side wall of the container; and inspecting means for inspecting the coplanarity of semiconductor package leads based on image data of the imaging means.

3. A semiconductor package inspection device, which images an upper surface and a side lead portion of a semiconductor package, and inspects the semiconductor package on the basis of image data thereof, characterized in that the semiconductor package inspection device comprises:

one visual camera means, which is provided above the semiconductor package, an imaging axis thereof being set at a proximate right angle relative to the upper surface of the semiconductor package, and which is set so that the upper surface of the semiconductor package is located in a center region of a field of view area thereof; and a light transmitting optical member, which has a predetermined refractive index, and which is provided between the semiconductor package and the visual camera means, a lead portion of the semiconductor package being imaged from diagonally above at a predetermined angle by the visual camera means, and an image thereof being guided to an edge portion region of the field of view area of the visual camera means, and that a thickness of the light transmitting optical member is set at a value, which absorbs an optical path length difference between an optical path from the upper surface of the semiconductor package to the visual camera means and an optical path from the side lead portion via the light transmitting optical member to the visual camera means.

4. The semiconductor package inspection device according to claim 3, further comprising:

a container for housing the semiconductor package; and lighting means for illuminating with a P polarizing wave the lead portion of the semiconductor package, wherein the imaging direction of the visual camera means is set to a Brewster angle relative to a side wall of the container.

5. The semiconductor package inspection device according to claim 3, wherein the light transmitting optical means is provided, or a portion of the light transmitting optical member is omitted, so as not to intervene in an optical path between the semiconductor package upper surface and a center region, of the field of view area of the visual camera means, where an upper surface image of the semiconductor package is imaged.

6. A semiconductor package inspection device, which inspects a coplanarity of leads of a semiconductor package housed in a predetermined container, characterized in that the semiconductor package inspection device comprises:

lighting means for illuminating with a P polarizing wave a lead portion of the semiconductor package;

one visual camera means, which is provided above the semiconductor package, an imaging axis thereof being set to a proximate right angle relative to an upper surface of the semiconductor package;

light guiding means, which is provided between the semiconductor package and the visual camera means, for guiding an image of the lead portion of the semiconductor package within a field of view of the visual camera means so that the lead portion of the semiconductor package is imaged from at least two different directions by the visual camera means, and further, one of imaging directions of the two imaging directions, is set to a Brewster angle relative to a side wall of the container; and inspecting means for inspecting the coplanarity of semiconductor package leads using a triangulation method based on image data of the imaging means.

7. The semiconductor package inspection device according to claim 6, wherein the light guiding means is a prism.

8. A semiconductor package inspection device, which images an upper surface and a side lead portion of a semiconductor package, and inspects the semiconductor package on the basis of image data thereof, characterized in that the semiconductor package inspection device comprises:

one visual camera means, which is provided above the semiconductor package, an imaging axis thereof being set at a proximate right angle relative to the upper surface of the semiconductor package, and which is set to that the upper surface of the semiconductor package is located in a center region of a field of view area thereof;

a light transmitting optical member, which has a predetermined refractive index, and which is provided between the semiconductor package and the visual camera means, a lead portion of the semiconductor package being imaged from at least two different directions by the visual camera means, and an image thereof being guided to an edge portion region of a field of view area of the visual camera means, and further, the light transmitting optical member either being provided, or a portion thereof being omitted, so as not to intervene in an optical path between the semiconductor package upper surface, and a center region of the field of view area of the visual camera means, where an upper surface image of the semiconductor package is imaged; and inspecting means for inspecting a coplanarity of semiconductor package leads using a triangulation method based on image data of the imaging means, and that a thickness of the light transmitting optical member is set at a value, which absorbs an optical path length difference between an optical path from the upper surface of the semiconductor package to the visual camera means and an optical path from the side lead portion via the light transmitting optical member to the visual camera means.

9. The semiconductor package inspection device according to claim 2, wherein the imaging means comprises:

one visual camera means, which is provided above the semiconductor package, an imaging axis thereof being set at a proximate right angle relative to the upper surface of the semiconductor package; and light guiding means, which is provided between the semiconductor package and the visual camera means, for guiding an image of a lead portion of the semiconductor package within a field of view of the visual camera means so that the lead portion of the semiconductor package is imaged from diagonally above at a predetermined angle by the visual camera means.

10. The semiconductor package inspection device according to claim 6, wherein the light guiding means is either a mirror or a prism.

11. The semiconductor package inspection device according to claim 2, wherein the container is an embossed tape.

12. The semiconductor package inspection device according to claim 4, wherein the light transmitting optical means is provided, or a portion of the light transmitting optical member is omitted, so as not to intervene in an optical path between the semiconductor package upper surface and a center region, of the field of view area of the visual camera means, where an upper surface image of the semiconductor package is imaged.

13. The semiconductor package inspection device according to claim 6, wherein the container is an embossed tape.

* * * * *